(12) United States Patent
Sahlberg et al.

(10) Patent No.: US 6,610,714 B2
(45) Date of Patent: Aug. 26, 2003

(54) NON-NUCLEOSIDE REVERSE TRANSCRIPTASE INHIBITORS

(75) Inventors: Christer Sahlberg, Hägersten (SE); Dmitry Antonov, Skogsås (SE); Hans Wallberg, Huddinge (SE); Rolf Noréen, Tullinge (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 10/093,112

(22) Filed: Mar. 5, 2002

(65) Prior Publication Data

US 2003/0092743 A1 May 15, 2003

(30) Foreign Application Priority Data

Aug. 28, 2001 (SE) .............................................. 0102867

(51) Int. Cl.[7] ...................... C07D 213/02; A61K 31/44; A61K 31/425

(52) U.S. Cl. ...................... 514/353; 514/371; 546/309; 548/194

(58) Field of Search .................... 546/309; 548/194; 514/353, 371

(56) References Cited

U.S. PATENT DOCUMENTS 3,803,175 A 4/1974 Sparks et al.

FOREIGN PATENT DOCUMENTS

| DE | 2041563 A | 3/1971 | |
|---|---|---|---|
| WO | WO 93/03022 | 2/1993 | |
| WO | WO 95/06034 | 3/1995 | |
| WO | WO 99/36406 | 7/1999 | |
| WO | WO 99/36406 A1 * | 7/1999 | ......... C07D/213/61 |
| WO | WO 99/47201 | 9/1999 | |
| WO | WO 00/39095 | 7/2000 | |
| WO | WO 00/47561 | 8/2000 | |
| WO | WO 00/56736 | 9/2000 | |
| WO | WO 00/78315 A1 | 12/2000 | |
| WO | WO 00/78721 A1 | 12/2000 | |
| WO | WO 00/78755 A1 | 12/2000 | |
| WO | WO 00/78756 A1 | 12/2000 | |

OTHER PUBLICATIONS

Kirmse et al, Journal of Organic Chemistry, vol. 53, No. 4, 1988, pp. 763–767.*
Derrick L.J. Clive et al., "Synthesis of (+)-puraquinonic acid: an inducer of cell . . . ," J. Org. Chem. 2001, 66, pp. 954–961. XP–002216804.
M.G. Kulkarni et al., "Synthesis of novel 3-allylbenzofurans via . . . , " Synthesis. 1997, 12, pp. 1420–1424. XP–001106509.
Biswajit Saha et al., "Intramolecular asymmetric cyclopropanation . . . ," Synlett. 2001, 1(1), pp. 114–116. XP–001106507.
Chi–Ming Che et al., "Asymmetric inter–and intramolecular cyclopropanation . . . ," J. Am. Chem. Soc. 2001, 123, pp. 4119–4129. XP–002216805.
Masakatsu Matsumoto et al., "o–Benzochinon–monoformylmethide durch . . . ," Angew. Chem. 1982, 94(5), pp. 376–377. XP002216806.
Andre Rosowsky et al., "2,4–Diaminothiene [2,3–d] pyrimidine analogue . . . ," J. Med. Chem. 1993, 36, pp. 3103–3112. XP–001106506.
Manik S. Sardessai et al., "The bromination of 2,5–dimethoyxbenzaldehyde . . . ," Organic Preparations and Procedures Int. 1991, 23(4), pp. 419–424. XP–002216807.
Takao Sakamoto et al., "Condensed heteroaromatic ring systems. . . ," Tetrahedron, 1991, 47(10), pp. 1877–1886. XP001106510.
Stephen F. Martin et al., "Iodocyclopropanes as Versatile Intermediates . . . ," Tetrahedron Letters, 1998, 39, pp. 1521–1524. XP002216808.
Tatsuya Uchida et al., "Co(II)–salen–catalyzed asymmetric intramolecular cyclopropanation . . . ," Tetrahedron Letters, 2001, 42, pp. 2521–2524. XP–002216809.

(List continued on next page.)

Primary Examiner—Zinna Northington Davis
(74) Attorney, Agent, or Firm—Birch, Stewart, Kolasch & Birch, LLP

(57) ABSTRACT

Compounds of the formula I:

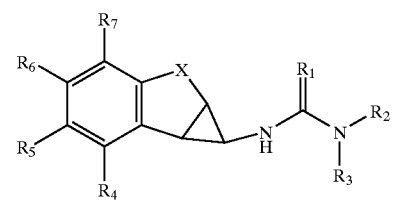

where;
  $R_1$ is O, S;
  $R_2$ is an optionally substituted nitrogen-containing heterocycle, wherein the nitrogen is located at the 2 position relative to the (thio)urea bond;
  $R_3$ is H, $C_1$–$C_3$ alkyl,
  $R_4$–$R_7$ are independently selected from H, $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbamoyl, cyano, halo, hydroxy, keto;
  X is —$(CR_8R_9)_n$—
  $R_8$ and $R_9$ are independently H, $C_1$–$C_3$ alkyl, OH or $R_8$ and $R_9$ together are $=O$
  n is 1, 2 or 3
and prodrugs and pharmaceutically acceptable salts thereof, have utility as inhibitors of HIV-1 reverse transcriptase, particularly drug escape mutants.

29 Claims, No Drawings

OTHER PUBLICATIONS

Yuki Takekawa et al., "Selective cleavage of the trisubstituted . . . ," Tetrahedron Letters, 1999, 40, pp. 6817–6820. XP–002216810.

Eric L. Dias et al., "Rhodium(I)–Catalyzed homologation of aromatic . . . ," J. Am. Chem. Soc. 2001, 123, pp. 2442–2443. XP–002216811.

Robert S. Coleman et al., "A covergent approach to the . . . ," Organic Letter, 2001, 3(8), pp. 1141–1144. XP–002216812.

Leticia Perez–Serrano et al., "Synthesis of tricyclic aromatic compounds by the . . . ," J. Org. Chem. 2000, 65, pp. 3513–3519. XP–002216813.

Gregory H. Merriman et al., "The Synthesis of N–(Pyridylamino)tetrahydroisoquinolines and . . . ," Synlett, 2000, 1, pp. 137–0139. XP001106583.

Arun K. Jain et al., "Some new constituents from . . . ,"J. Indian Chem. Soc., Aug. 1991, pp. 452–454. XP–002216814.

Reckendorf, W. Meyer eta l.; "Synthesis of Methyl 4, 6–O–Benzylidene–2, 3–, . . . " Angew. Chem. Internat. Edit. vol. 7 (1968) No. 2.

Reckendorf, W. Meyer et al., "Synthese von. 2.3–[2–Amino–athyliden] . . . " Chem. Ber. 105, 686–695 (1972).

Hogberg, Marita et al.; "Urea–PETT Compounds as a New Class . . . " J. Med. Chem. 1999, 42, 4150–4160.

Cantrell, Amanda S. et al.; "Phenethylthiazolythiourea (PETT) Compounds . . . " J. Med. Chem. 199, 39, 4261–4274.

Bell, Frank W. et al.; "Phenethylthiazolethiourea (PETT) Compounds, a New Class of . . . " Reprinted from Journal of Medical Chemistry, 1995, 38, pp. 4929–4936.

Kirmase, Wolgang et al.; "Carbenes and the O–H Bond: . . ." J. Org. Chem. 1988, 53, 763–767.

\* cited by examiner

NON-NUCLEOSIDE REVERSE TRANSCRIPTASE INHIBITORS

This nonprovisional application claims priority under 35 U.S.C. §119(a) on patent application Ser. No. 0102867.9 filed in Sweden on Aug. 28, 2001, which is herein incorporated by reference.

TECHNICAL FIELD

This invention relates to non-nucleoside reverse transcriptase inhibitors active against HIV-1 and having an improved resistance profile. The invention further relates to the synthesis of such compounds and their use in antiviral methods and compositions.

BACKGROUND TO THE INVENTION

Non nucleoside reverse transcriptase inhibitors (NNRTI) bind to an allosteric site on reverse transcriptase and represent an important development in the arsenal of drugs against HIV, particularly HIV-1. International patent application WO 93/03022, discloses thiourea NNRTI which were later denoted "PETT" (phenyl ethyl thiazolyl thiourea) compounds in J Med Chem 39 6 1329–1335 (1995) and J Med Chem 39 21 4261–4274 (1996). International patent application nos. WO99/47501, WO/0039095, WO/0056736, WO00/78315 and WO00/78721 describe thiourea PETT derivatives which have allegedly been optimised against a composite RT binding pocket.

International patent application no WO95/06034 and J Med Chem 42 4150–4160 (1999) disclose urea isosteres of PETT NNRTIs. International patent application no WO99/36406 discloses urea NNRTI compounds with a freestanding cyclopropyl bridge, wherein the phenyl right hand wing bears an obligate 6-hydroxy function and international patent application no WO 00/47561 discloses prodrugs of such compounds.

Although the urea and thiourea NNRTI disclosed in the above documents are extremely active against reverse transcriptase, especially that of HIV-1, the nature of the HIV virus with its extreme lack of replicative fidelity and consequent tendency to rapid resistance development prompts a demand for further antiretroviral agents with enhanced antiviral performance against problematic drug escape mutants, notably at the RT 100, 103 and/or 181 positions.

Additionally, modern HIV therapy regimes, denoted HAART, Highly Active Anti Retroviral Therapy, administer antivirals as combinations of three or more antivirals of various classes, which combinations are administered for prolonged periods, if not for life. HAART requires the patient to follow a complicated dosing schedule with sometimes dozens of tablets per day taken at various times of the day in some cases before and in other cases after the ingestion of food. There is thus a need for antiretroviral preparations allowing greater flexibility in dosing to facilitate patient compliance.

BRIEF DESCRIPTION OF THE INVENTION

In accordance with a first aspect of the invention there are provided compounds of the formula I:

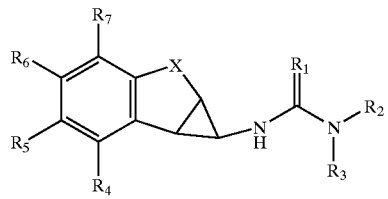

where;
$R_1$ is O, S;
$R_2$ is an optionally substituted, nitrogen-containing heterocycle, wherein the nitrogen is located at the 2 position relative to the (thio)urea bond;
$R_3$ is H, $C_1$–$C_3$ alkyl,
$R_4$–$R_7$ are independently selected from H, $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbamoyl, cyano, halo, hydroxy, keto and the like;
X is —(CR8R9)$_n$—
$R_8$ and $R_9$ are independently H, $C_1$–$C_3$ alkyl, OH or $R_8$ and $R_9$ together are =O
n is 1, 2 or 3
and pharmaceutically acceptable salts and prodrugs thereof.

The currently preferred value for R1 is O that is a urea derivative, although $R_1$ as S (ie a thiourea derivative) is also highly potent.

Representative values for R2 include thiazolyl, pyridyl, pyrimidyl, pyrazinyl, pyridazinyl, pyrrolyl, imidazolyl, indolyl, triazolyl, tetrazolyl, piperidyl, piperazinyl and fused rings such as benzothiazolyl, benzopyridyl, benzodiazolyl, benzimidazolyl, quinolyl, purinyl and the like, any of which can be optionally substituted.

Preferred $R_2$ values include pyrid-2-yl and thiazol-2-yl.

The optional substituents to R2 can include up to three substituents such as $C_1$–$C_6$ alkyl, $C_1$–$C_6$ alkoxy, $C_2$–$C_6$ alkenyl, $C_2$–$C_8$ alkynyl, $C_2$–$C_8$ alkenoxy, $C_1$–$C_6$ alkoxy $C_1$–$C_6$ alkyl, $C_1$–$C_6$ alkanoyl, halo$C_1$–$C_6$ alkyl, $C_1$–$C_4$ alkanoyloxy, $C_1$–$C_4$ alkylthio, amino (including $C_1$–$C_3$ alkyl-substituted amino), carboxy, carbamoyl, cyano, halo, hydroxy, aminomethyl, carboxymethyl, hydroxymethyl, nitro, aryl, (such as phenyl, pyrrol-1-yl, tetrazol-5-yl, triazol-4-yl, pyridyl, pyrimidyl, pyrazinyl, pyridazinyl, imidazolyl, indolyl, piperidyl, piperazinyl substituted (as herein defined) aryl, or —SO$_2$Q or —C(=O)Q, where Q is $C_1$–$C_6$ alkyl, halosubstituted $C_1$–$C_6$ alkyl, aryl (as herein defined), substituted (as herein defined) aryl or amino. Heteroatoms in R2 can be derivatised, such as with $C_1$–$C_6$ alkyl, oxo and the like. The optional $R_2$ substituent may be ortho or meta to the bond to the (thio)urea function but is preferably para, for example at the 5 position of pyrid-2-yl.

Preferred optional substituents to $R_2$ include cyano, halo, (especially fluoro, iodo and particularly chloro and bromo), phenoxy, pyrrid-1-yl and dimethylamino.

The currently preferred value for $R_3$ is H.

Preferably $R_4$ is hydrogen, halo or hydroxy, especially fluoro.

Preferably $R_5$ is halo, $C_{1-3}$ alkylcarbonyl, C1–3alkyloxy or H, especially fluoro and most preferably H.

Preferably $R_6$ is hydrogen, halo, $C_1$–$C_3$alkyloxy, C1–3alkylcarbonyl, cyano or ethynyl, especially methoxy or fluoro and most preferably H.

Preferably $R_7$ is hydrogen, halo, $C_{1-3}$alkyloxy, or $C_{1-3}$alkylcarbonyl, most preferably fluoro.

Preferably $R_5$ and $R_6$ are H and $R_4$ and $R_7$ are halo, most preferably both are fluoro.

The compounds of formula I may be administered as a racemic mixture, but preferably the cyclopropyl moiety intermediate the (thio)urea function, X and the phenyl ring (denoted Y below) is at least 75% such as around 90% enantiomerically pure with respect to the conformation:

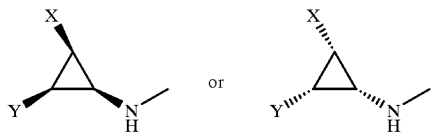

Although not wishing to be bound, on the basis of preliminary x-ray crystallography of structurally analogous compounds a presently favoured absolute configuration is likely to be:

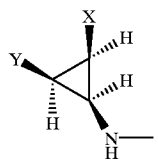

The currently preferred values for n are 1 (that is am indane derivative) or 2 (that is a tetralin derivative). Conveniently each R8 and R9 are H. A further preferred alternative is where a single pair of R8 and R9 may together define =O, and any further R8 and R9 groups are H.

$C_1$–$C_n$ alkyl where n is 3,6,7 etc or lower alkyl includes such groups as methyl, ethyl, n-propyl, isopropyl, n-butyl, s-butyl, t-butyl, n-pentyl, n-hexyl, 3-methyl pentyl and the like. The term halo refers to chloro, bromo, fluoro and iodo. $C_1$–$C_n$ alkoxy refers to groups such as methoxy, ethoxy, propoxy, t-butoxy and the like. $C_2$–$C_n$ alkenyl,refers to groups such as vinyl, 1-propen-2-yl, 1-buten-4-yl, I-penten-5-yl, 1-buten-1-yl and the like. $C_1$–$C_n$ alkylthio includes methylthio, ethylthio, t-butylthio and the like. $C_1$–$C_n$ alkanoyloxy includes acetoxy, propionoxy, formyloxy, butyryloxy and the like. $C_2$–$C_n$ alkenoxy includes ethenyloxy, propenyloxy, iso-butoxyethenyl and the like. Halo$C_1$–$C_n$ alkyl includes alkyls as defined herein substituetd 1 to 3 times by a halogen including trifluormethyl, 2-dichloroethyl, 3,3-difluoropropyl and the like. The term amine includes goups such as $NH_2$, NHMe, $N(Me)_2$ which may optionally be substituted with halogen, $C_1$–$C_7$ acyloxy, $C_1$–$C_6$ alkyl, $C_1$–$C_6$ alkoxy, nitro, carboxy, carbamoyl, carbamoyloxy cyano, methylsulphonylamino and the like. Carboxy, carboxymethyl and carbamoyl include the corresponding pharmaceutically acceptable $C_1$–$C_6$ alkyl and aryl esters.

Prodrugs of the compounds of formula I are those compounds which following administration to a patient release a compound of the formula I in vivo. Typical prodrugs are pharmaceutically acceptable ethers and especially esters including phosphate esters) when any of $R_4$–$R_7$ or the optional substituent to $R_2$ represent an hydroxy function, pharmaceutically acceptable amides or carbamates when any of the $R_2$ substituent or $R_4$–$R_7$ represent an amine function or pharmaceutically acceptable esters when the $R_2$ substituent or $R_4$–$R_7$ represent a carboxy function.

Hydroxy protecting group as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The invention further provides pharmaceutical compositions comprising the compounds of the invention and pharmaceutically acceptable carriers or diluents therefor. Additional aspects of the invention provide methods for the inhibition of HIV comprising administering a compound of the formula I to a subject afflicted with HIV. The invention also extends to the use of the compounds of formula I in therapy, such as in the preparation of a medicament for the treatment of HIV infections.

In treating conditions caused by HIV, the compounds of formula I are preferably administered in an amount to achieve a plasma level of around 10 to 1000 nM and more preferably 100 to 500 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500–750 mg, in one to four dosage units per day.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, abacavir, adefovir, adefovir dipivoxil, bis-POC-PMPA, foscarnet, GW420 876X, hydroxyurea, Hoechst-Bayer HBY 097, efavirenz, trovirdine, capravirine, nevirapine, delaviridine, tipranovir, emtricitabine, PFA, H2G (omaciclovir), MIV-606 (valomaciclovir stearate) TMC-126, TMC-125, TMC-120, DMP-450, loviride, ritonavir (includinge kaletra) lopinavir, saquinavir, indinavir, lasinavir, amprenavir, amprenavir phosphate, nelfinavir and the like, typically at molar ratios reflecting their respective activities and bioavailabilities. Generally such ratio will be of the order of 25:1 to 1:25, relative to the compound of formula 1.

Compounds of the invention are typically prepared as follows:

Scheme 1

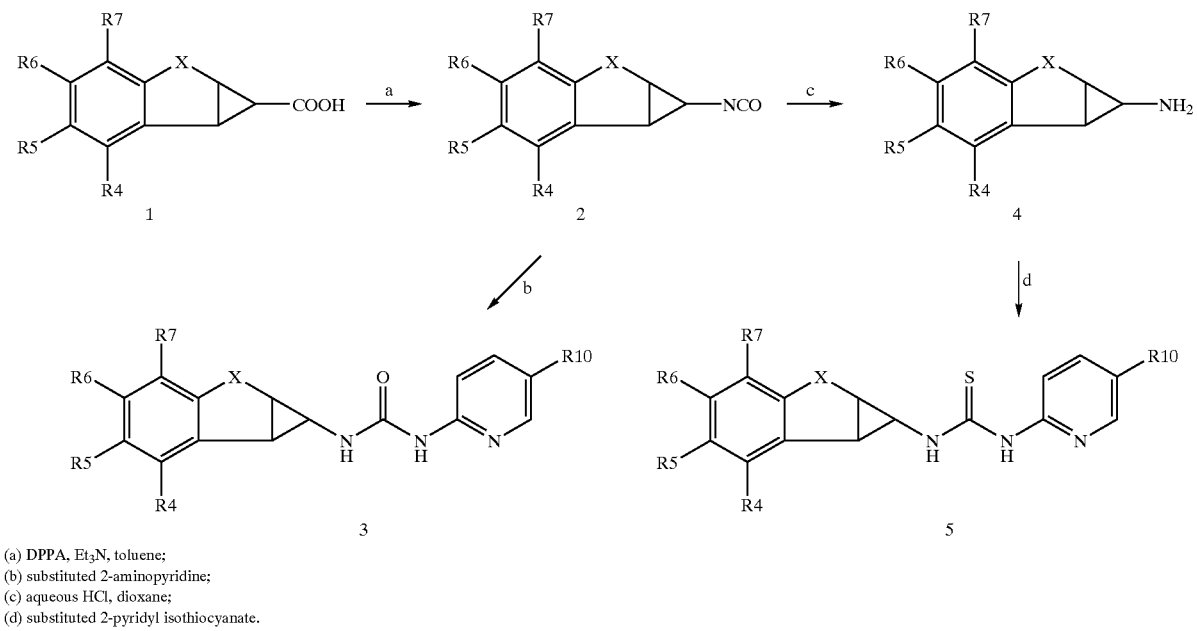

(a) DPPA, Et₃N, toluene;
(b) substituted 2-aminopyridine;
(c) aqueous HCl, dioxane;
(d) substituted 2-pyridyl isothiocyanate.

Compounds of the general formula (I), wherein R1 is O (urea) or S (thiourea), R2 is, for example, a 5-substituted pyrid-2-yl, and R3 is H, are prepared by methods shown in Scheme 1. The cyclopropanecarboxylic acid 1-Scheme-1 is converted to the acyl azide and heated to 120° C. to induce Curtius rearrangement and provide the isocyanate 2-Scheme-1. The urea 3-Scheme-1 is obtained by coupling of the isocyanate with the relevantly substituted 2-aminopyridine. Hydrolysis of the isocyanate as in step (c) which results in the cyclopropylamine 4-Scheme-1, followed by reaction with a 2-pyridyl isothiocyanate provides the thiourea 5-Scheme-1. The isothiocyanate may be prepared from the substituted 2-aminopyridine (or other appropriate R2 amine) by known methods, such as treatment with thiophosgene or thiocarbonyldiimidazole. Specially synthesized 2-aminopyridines, otherwise commercially available or whose preparations are described in literature, are shown in Scheme 2. $R_1$=S compounds can alternatively be prepared from the isothiocyanate corresponding to 2-Scheme 2 or from amine 3-Scheme 2 and amino-$R_2$ in conjunction with an RC(=S)R' both as described in WO 9303022. Although scheme 1 has been illustrated with a substituted pyridyl it is readily apparent that corresponding couplings can be used for other $R_2$ variants such as optionally substituted thiazolyl, pyrazinyl, benzothiazolyl, pyrimidinyl etc.

Scheme 2

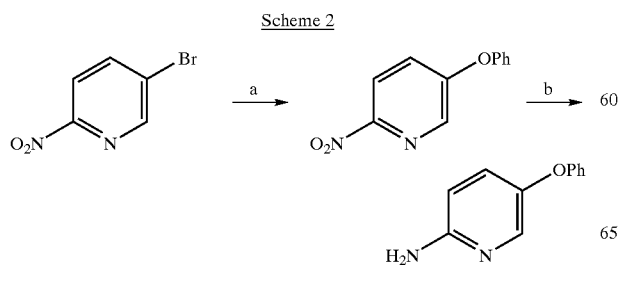

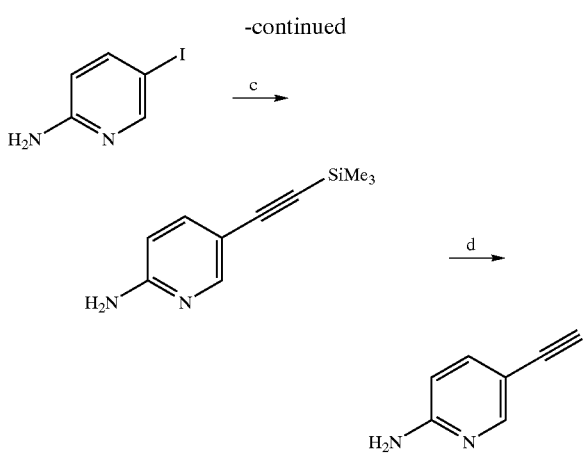

(a) phenol, NaH, DMF;
(b) 10% Pd/C, H₂ 1 atm, EtOH;
(c) PdCl₂(PPh₃)₂, trimethylsilylacetylene, CuI, diisopropylamine;
(d) tert-butylammonium fluoride Replacement of the bromine in 5-bromo-2-nitropyridine by a phenoxy group, followed by reduction of the nitro group affords the 2-amino-5-phenoxypyridine. The Sonogashira coupling of 2-amino-5-iodopyridine with the terminal alkyne SiMe₃C≡CH in the presence of catalytic amounts of bis(triphenylphosphine)palladium dichloride and cuprous iodide as in step (c) provides the 2-amino-5-(2-trimethylsilylethynyl)pyridine. Removal of the silyl group by TBAF yields 2-amino-5-ethynylpyridine which can be coupled to the isocyanate as described in Scheme 1. Alternatively, treatment with TBAF may be performed on the urea 3-Scheme-1 or thiourea 5-Scheme-1 where R10 is —C≡CSiMe₃ to convert R10 to —C≡CH.

Scheme 3

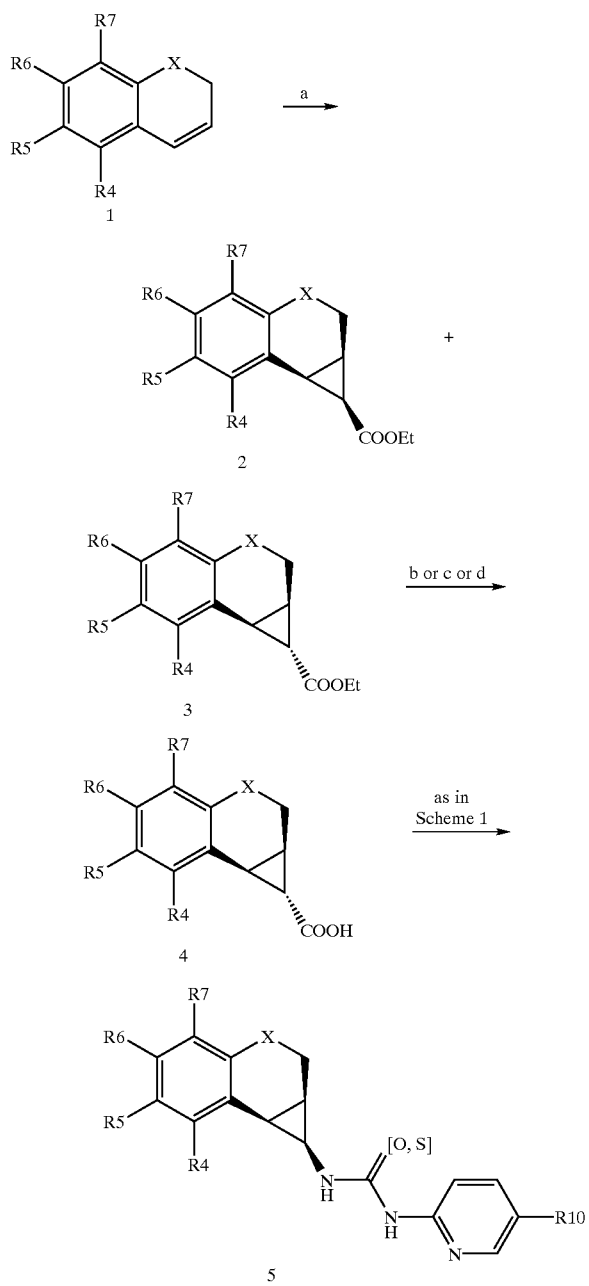

(a) ethyl diazoacetate, catalyst, CH$_2$Cl$_2$;
(b) chromatograhy and then reflux with LiOH, H$_2$O, MeOH;
(c) reflux with LiOH, H$_2$O, MeOH and then chromatography;
(d) rt, NaOH, H$_2$O, MeOH and then reflux with LiOH, H$_2$O, MeOH Compounds of the general formula (I), wherein R1 is O (urea) or S (thiourea), R2 is, for example, a 5-substituted pyrid-2-yl, R3 is H, X is optionally substitued methylene, ethylene or propylene, and wherein the cyclopropyl moiety has the relative configuration:

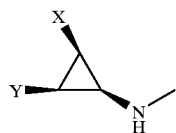

are prepared by methods shown in Scheme 3. Cyclopropanation of the double bond in the tetralin 3 (or 5/7 ringed homologue) with ethyl diazoacetate is catalyzed by cuprous or rhodium(II) salts such as CuI, (CuOTf)$_2$-benzene, and Rh$_2$(OAc)$_4$ in solvents such as dichloromethane, 1,2-dichloroethane, or chloroform. The reaction provides a diastereomeric mixture of the cyclopropanecarboxylic acid ethyl esters 2-Scheme-3, with the all cis relative configuration, and its trans isomer 3-Scheme-3. Separation by column chromatography of the cis and trans diastereomers may be accomplished at this stage, followed by hydrolysis of the isolated 2-Scheme-3, such as by refluxing in aqueous methanolic LiOH, to yield a racemic mixture of the all cis cyclopropanecarboxylic acid 4-Scheme-3, as described in step (b). Alternatively, the diastereomeric mixture of ethyl esters may be subjected to hydrolysis, and separation conducted on the mixture of cyclopropanecarboxylic acids to provide the isolated all cis isomer, as in step (c). Step (d) involves isolation of the cis ethyl ester 2-Scheme-3 which may also be done by selective hydrolysis of the trans 3-Scheme-3 at lower temperatures, such as treatment with aqueous methanolic NaOH at ambient temperature. The isolated cis ethyl ester may then be hydrolyzed in the usual manner to the cyclopropanecarboxylic acid 4-Scheme-3. The cyclopropanecarboxylic acid is subjected to the methods outlined in Scheme 1 to obtain the urea or thiourea 5-Scheme-3. The tetralin/homologues 1-Scheme-3 are prepared by methods shown in Scheme 4.

Scheme 4

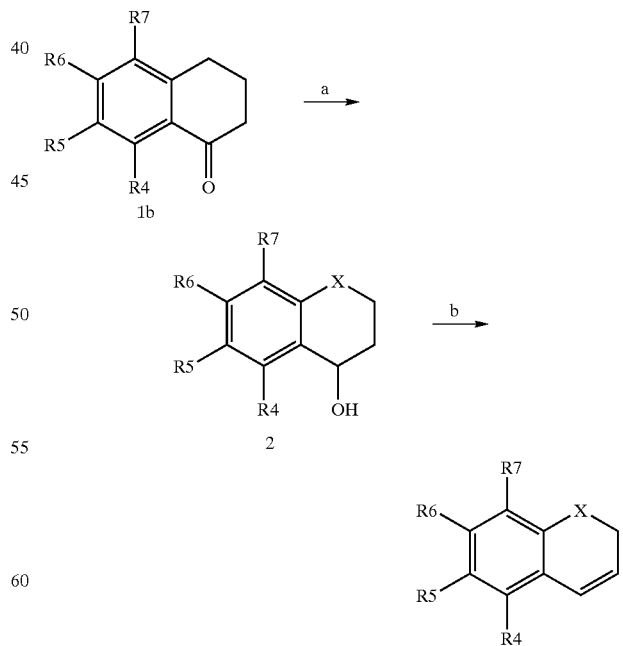

(a) NaBH$_4$, EtOH;
(b) p-toluenesulfonic acid, toluene, reflux;

Scheme 4 describes the preparation of tetralins, indanes and homologues, used as starting material in Scheme 3, from known monosubstituted tetralones etc, wherein only one of the positions in R4 to R7 is substituted with halo or $C_{1-3}$ alkoxy. Conversion of the carbonyl group in 1-tetralone 1b-Scheme-4 to the correponding alcohol by a suitable reducing agent such sodium borohydride in ethanol provides 2-Scheme-4. Refluxing the alcohol with small amounts of acid, such as p-TsOH in toluene, causes dehydration of 2-Scheme-4 to the desired tetralin 1-Scheme-3. Corrresonding reactions are applicable to n=1 or 3.

The compounds of the invention can form salts which form an additional aspect of the invention. Appropriate pharmaceutically acceptable salts of the compounds of Formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The compounds of the invention I may in some cases be isolated as the hydrate.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

DETAILED DESCRIPTION

Various aspects of the invention will now be illustrated by way of example only with reference to the following non-limiting examples.

EXAMPLE 1

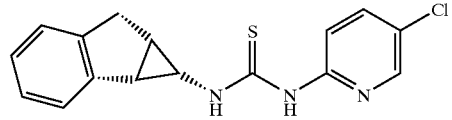

a) 1,1 a,66a-tetrahydrocyclopropa[a] indene-1-carboxylic acid ethyl ester

Indene is diluted in 100 ml dichloroethane. Around 10 mg of CuI and around 10 mg Pd(OAc)$_2$ is added. 25 ml of the resultant mixture is dropwise added to 25 ml ethyldiazoacetate and refluxed for 30 minutes . The solution is filtered through Al$_2$O$_3$ which is eluted with a EtOAC/hexane gradient. The eluate is evaporated vigorously at 100°, 2mmHg to yield the title compound (36 g).

b) 1,1 a,66a-tetrahydrocyclopropa[a] indene-1-amine

The product of step a) is boiled with around 50 g NaOH in 200 ml 10:1 MeOH:H$_2$O for 2 hours. The mixture is diluted with water, washed with dichloroethane, evaporated with HOAc, extracted with dichloroethane, washed with wated, dried with sulphate, filtered and evaporated to yield 25 g of the acid, 95% pure. DPPA 275.2 δ=1.128 10 ml, 46.5 mmol TEA 7.1 ml 1.1ee and 7.3 g of the acid (mass 174.12, 0.9ee) is mixed in 200 ml toluene and refluxed for around 2 hours. The product is evaporated and dissolved in dioxane 200 ml. 25 ml HCl(aq) and 25 ml water is added and the mixture agitated for 60 minutes at room temperature. The solution is partioned with acid/base in water/dichloroethane. The organic phase is dired, filtered and evaporated. The product is chromatographed through a silica 60 column to yield 660 mg of 85% pure cis amine, mol wt 145.11.

c) Imidazole-1-carbothioic acid (5-chloro-pyridin-2-yl)amide 60 g N,N-thiocarbodiidazole is dissolved in 500 ml acetonitrile at 400°. 43 g 2-amino-5-chlorpyridine is added and the mixture stirred at room temperature overnight, filtered and dried.

d) The activated product of step c (600 mg, 2 mmol) and the product of step b) 300 mg, 2.1 mmol are coupled as described in EP 540 143 to yield 0.55 g of the title compound.

EXAMPLE 2

±cis-1-(5-Cyano-pyridin-2-yl)-3-(1,1a,6,6a-tetrahydro-cyclopropa[a]inden-1-yl)-urea.

a) ±cis-1,1a,6,6a-Tetrahydro-cyclopropa[a]indene-1-carboxylic acid ethyl ester

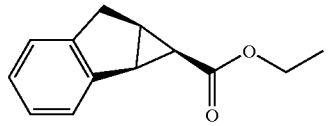

To a mixture of indene (11.6 g, 100 mmol) and Cu$_2$Br$_2$ (0.10 g, 0.35 mmol) in 1,2-dichloroethane (200 mL) at 80° C., was added dropwise (3h) a solution of ethyl diazoacetate (17.1 g, 150 mmol) in 1,2-dichloroethane (35 mL). After 15 min at 80° C., the reaction mixture was washed with H$_2$O (200 mL). The H$_2$O phase was washed with CH$_2$Cl$_2$ (50 mL) and the solvent of the combined organic phases was removed under reduced pressure. The crude product was column chromatographed (silica gel, 5→10% EtOAc in Hexane), to give 3.63 g (18%) of ±cis-1,1a,6,6a-tetrahydro-cyclopropa[a]indene-1-carboxylic acid ethyl ester and 6.68 g (33%) of ±trans-1,1a,6,6a-tetrahydro-cyclopropa[a]indene-1-carboxylic acid ethyl ester as a byproduct.

$^1$H-NMR (CDCl$_3$): 7.30–7.05 (m, 4H), 3.81 (q, 2H), 3.36 (d, 1H), 3.18 (dd, 1H), 2.92 (m, 1H), 2.24 (m, 1H), 1.99 (dd, 1H), 0.92 (t, 3H).

b) ±cis-1,1a,6,6a-Tetrahydro-cyclopropa[a]indene-1-carboxylic acid

±cis1,1a,6,6a-Tetrahydro-cyclopropa[a]indene-1-carboxylic acid was synthesized from ±cis1,1a,6,6a-tetrahydro-cyclopropa[a]indene-1-carboxylic acid ethyl ester (3.53 g, 15.5 mmol), LiOH (539 mg, 22.5 mmol), H$_2$O (10 mL) and MeOH (20 mL) which were heated to reflux for 2h, concentrated and acidified to precipitate 1.62 g (62%) of ±cis-1,1a,6,6a-tetrahydro-cyclopropa[a]indene-1-carboxylic acid as a white solid. The product was not crystallized.

$^1$H-NMR (CDCl$_3$): 10.95 (br s, 1H), 7.35–7.02 (m, 4H), 3.29 (d, 1H), 3.14 (dd, 1H), 2.96 (m, 1H), 2.27 (m, 1H), 1.91 (dd, 1H).

c) ±cis-1-(5-Cyano-pyridin-2-yl)-3-(1,1a,6,6a-tetrahydro-cyclopropa[a]inden-1-yl)-urea

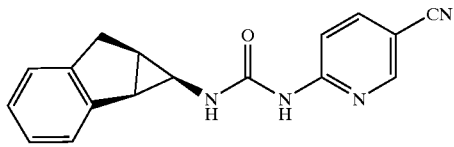

±cis-1-(5-Cyano-pyridin-2-yl)-3-(1,1 a,6,6a-tetrahydro-cyclopropa[a]inden-1-yl)-urea was synthesized from ±cis-1,1a,6,6a-tetrahydro-cyclopropa[a]indene-1-carboxylic acid (261 mg, 1.5 mmol) and triethylamine (209 µL, 1.5 mmol) in toluene (1.5 mL) at 20° C., to which was added diphenylphosphoryl azide (413 mg, 1.5 mmol). After 30 min at 20° C., the reaction mixture was heated to 120 20° C. for 15 min, where after a solution of 2-amino-5-cyano-pyridine (197 mg, 1.65 mmol) in DMF (1mL) was added. After 3h at 120° C., the reaction mixture was allowed to assume room temperature. The reaction mixture was concentrated under reduced pressure, benzene (20 mL) was added and the reaction mixture was washed with 1 N HCl (30 mL), H$_2$O (30 mL) and brine (30 25 mL). The solvent of the organic phases was removed under reduced pressure. The crude product was column chromatographed (silica gel, 4→5% MeOH in CH$_2$Cl$_2$), to give 25 mg (5%) of ±cis-1-(5-cyano-pyridin-2-yl)-3-(1,1a,6,6a-tetrahydro-cyclopropa[a]inden-1-yl)-urea.

$^1$H-NMR (DMSO-d$_6$): 9.58 (s, 1H), 8.18 (d, 1H), 7.96 (dd, 1H), 7.40–7.25 (m, 3H), 7.17–7.05 (m, 3H), 3.27–3.13 (m, 2H), 2.80–2.73 (m, 2H), 2.05 (dd, 1H).

EXAMPLE 3

±cis-1-(5-Cyano-pyridin-2-yl)-3-(1a,2,3,7b-tetrahydro-cyclopropa[a]naphthalen-1-yl)-urea a) 1a,2,3,7b-Tetrahydro-1H-cyclopropa[a]naphthalene-1-carboxylic acid ethyl ester

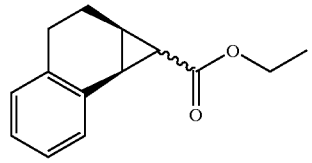

1a,2,3,7b-Tetrahydro-1H-cyclopropa[a]naphthalene-1-carboxylic acid ethyl ester was synthesized analogously to Example 2 from 1,2-dihydronaphthalene (3.91 g, 30 mmol), to give 688 mg (11%) of 1a,2,3,7b-tetrahydro-1H-cyclopropa[a]naphthalene-1-carboxylic acid ethyl ester (a 56/39 mixture of cis and trans isomers).

$^1$H-NMR (CDCl$_3$): 7.35–6.95 (m, 4H), 4.30–3.85 (m, 2H), 2.90–1.00 (m, 10H).

b) 1a,2,3,7b-Tetrahydro-1H-cyclopropa[a]naphthalene-1-carboxylic acid

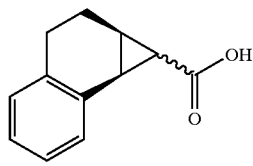

1a,2,3,7b-Tetrahydro-1H-cyclopropa[a]naphthalene-1-carboxylic acid was synthesized analogously to Example 2b from 1a,2,3,7b-tetrahydro-1H-cyclopropa[a]naphthalene-1-carboxylic acid ethyl ester (688 mg, 3.18 mmol, a 56/39 mixture of cis and trans isomers), to give 540 mg (90%) of 1a,2,3,7b-tetrahydro-1H-cyclopropa[a]naphthalene-1-carboxylic acid (a 56/39 mixture of cis and trans isomers). The product was not crystallized.

$^1$H-NMR (CDCl$_3$): 11.36 (br s, 1H), 7.30–6.95 (m, 4H), 2.80–1.65 (m, 7H).

c) ±cis-1-(5-Cyanopyridin-2-yl)-3-(1a,2,3,7b-tetrahydro-cyclopropa[a]naphthalen-1-yl)-urea.

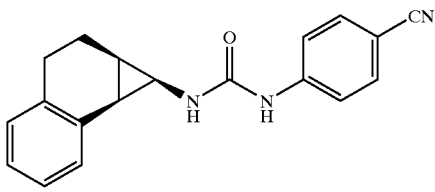

±cis-1-(5-Cyanopyridin-2-yl)-3-(1a,2,3,7b-tetrahydro-cyclopropa[a]naphthalen-1-yl)-urea was synthesized analogously to Example 2c from ±cis-1a,2,3,7b-tetrahydro-1H-cyclopropa[a]naphthalene-1-carboxylic acid (471 mg, 2.5 mmol, a 56/39 mixture of cis and trans isomers). The crude product was column chromatographed (silica gel, 4→5% MeOH in CH$_2$Cl$_2$), to give 80 mg (11%) of ±cis-1-(5-cyanopyridin-2-yl)-3-(1a,2,3,7b-tetrahydro-cyclopropa[a]naphthalen-1-yl)-urea and 32 mg (4.2%) of ±-trans-1-(5-cyanopyridin-2-yl)-3-(1a,2,3,7b-tetrahydro-cyclopropa[a]naphthalen-1-yl)-urea as a byproduct.

$^1$H-NMR (DMSO-d$_6$): 9.70 (s, 1H), 8.14 (d, 1H), 7.99 (dd, 1H), 7.45 (d, 1H), 7.38 (br s,1H), 7.30–7.00 (m, 4H), 3.10 (ddd, 1H), 2.75–2.60 (m, 1H), 2.60–2.40 (m, 1H), 2.21 (dd, 1H), 1.98 (m, 1H), 1.85–1.55 (m, 2H).

EXAMPLE 4

±cis-1-(5-Cyanopyridin-2-yl)-3-(1,1a2,3,4,8b-hexahydro-benzo[a]cyclopropa[c]cyclohepten-1-yl)-urea a) 1,1a,2,3,4,8b-Hexahydro-benzo[a]cyclopropa[c]cycloheptene-1-carboxylic acid ethyl ester

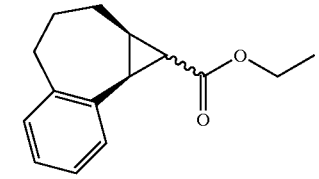

1,1a,2,3,4,8b-Hexahydro-benzo[a]cyclopropa[c]cycloheptene-1-carboxylic acid ethyl ester was synthesized analogously to Example 2a from 6,7-dihydro-5H-benzocycloheptane (4.40 g, 30.5 mmol), to give 3.43 g (49%) of 1,1a,2,3,4,8b-hexahydro-benzo[a]cyclopropa[c]cycloheptene-1-carboxylic acid ethyl ester (a 1/10 mixture of cis and trans isomers).

$^1$H-NMR (CDCl$_3$): 7.40–6.90 (m, 4H), 4.30–4.00 (m, 2H), 3.30–0.50 (m, 12H).

b) 1,1a,2,3,4,8b-Hexahydro-benzo[a]cyclopropa[c]cycloheptene-1-carboxylic acid.

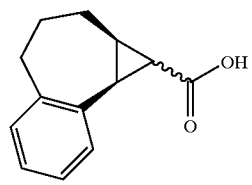

1,1a,2,3,4,8b-Hexahydro-benzo[a]cyclopropa[c]cycloheptene-1-carboxylic acid was synthesized analogously to Example 2 from 1,1a,2,3,4,8b-hexahydro-benzo[a]cyclopropa[c]cycloheptene-1-carboxylic acid ethyl ester (3.43 g, 14.9 mmol, a 1/10 mixture of cis and trans isomers), to give 2.81 g (93%) of 1,1a,2,3,4,8b-hexahydro-benzo[a]cyclopropa[c]cycloheptene-1-carboxylic acid (a 1/10 mixture of cis and trans isomers). The product was not crystallized.

$^1$H-NMR (CDCl$_3$): 10.76 (br s, 1H), 7.40–7.00 (m, 4H), 3.30–0.50 (m, 9H).

c) ±cis-1-(5-Cyanopyridin-2-yl)-3-(1,1a,2,3,4,8b-hexahydro-benzo[a]cyclopropa[c]cyclohepten-1-yl)-urea

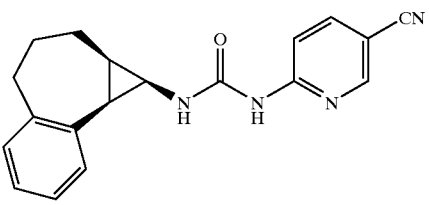

±cis-1-(5-Cyanopyridin-2-yl)-3-(1,1a,2,3,4,8b-hexahydro-benzo[a]cyclopropa[c]cyclohepten-1-yl)-urea was synthesized analogously to Example 2 from ±cis-1,1a,2,3,4,8b-hexahydro-benzo[a]cyclopropa[c]-cycloheptene-1-carboxylic acid (809 mg, 4 mmol, a 1/10 mixture of cis and trans isomers). The crude product was column chromatographed (silica gel, 4→5% MeOH in $CH_2Cl_2$), to give 30 mg (2.4%) of ±cis-1-(5-cyano-pyridin-2-yl)-3-(1,1 a,2,3,4,8b-hexahydro-benzo[a]cyclopropa[c]cyclohepten-1-yl)-urea and 170 mg (13%) of ±trans-1-(5-cyano-pyridin-2-yl)-3-(1,1a,2,3,4,8b-hexahydro-benzo[a]cyclopropa[c]cyclohepten-1-yl)-urea as a byproduct.

$^1$H-NMR (DMSO-$d_6$): 9.90 (s, 1H), 8.37 (d, 1H), 8.05 (dd, 1H), 7.78 (br s, 1H), 7.45 (d,1H), 7.30–7.08 (m, 4H), 3.23–3.09 (m, 2H), 2.57 (m,1H), 2.25 (dd, 1H), 2.00–1.75 (m, 1H), 1.75–1.45 (m, 2H), 1.35–1.20 (m, 1H), 0.75–0.50 (m, 1H).

Example 5

+/−cis-N-(5-cyano-2-pyridinyl)-N-(5-methoxy-1a,2,3,7b-tetrahydro-1H-cyclopropa[a]naphthalen-1-yl)urea a) 6-methoxy-1,2,3,4-tetrahydronaphthalen-1-ol

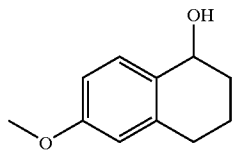

6-Methoxytetralone (10 g, 0.057 mol) was mixed with 150 ml of dry ethanol and sodium borohydride (1.2 eq) was added by portions to the stirred mixture. The reaction mixture was left to stir at ambient temperature for 15 h. The reaction mixture was then concentrated by rotary evaporation, mixed with 100 ml of water and heated for 1 h at 45° C.. The resulting mixture was extracted into diethyl ether (3×80 ml). Combined organic extract was dried over $Na_2SO_4$ and concentrated by rotary evaporation to give 10.39 g of yellow oil which was used in the next step without additional purification.

b) 7-methoxy-1,2-dihydronaphthalene

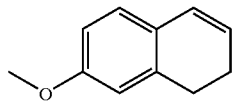

Crude 6-methoxy-1,2,3,4-tetrahydronaphthalen-1-ol (10.3 g, 0.058 mol) was dissolved in 100 ml of toluene and heated in an oil bath (115° C.). P-tolylsulphonic acid (20 mg) was added to the reaction mixture and it was refluxed for about 1 h. The reaction was monitored by GC. The reaction mixture was then cooled and washed with sat. $NaHCO_3$ solution, water and brine and organic layer was dried over $Na_2SO_4$. Concentration gave 8.87 g of light brown oil. Yield 96%.

c) Ethyl 5-methoxy-1a,2,3,7b-tetrahydro-1H-cyclopropa[a]naphthalene-1-carboxylate

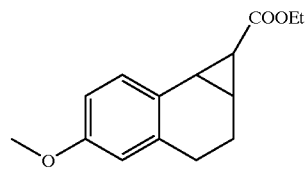

7-Methoxy-1,2-dihydronaphthalene (8.8 g, 0.055 mol) was mixed with 1 ml of degassed absolute methylene chloride and 20 mg of rhodium acetate (appr. 0.1 mol %). The reaction mixture was bubbled with nitrogen and ethyl diazoacetate (2 eq, 50% solution in degassed abs. methylene chloride) was added slowly through the syringe (flow rate about 1 ml/hour) to the stirred solution at ambient temperature. Gas evolution started upon the addition. The reaction was monitored by GC. Additional amount of catalyst was added during the reaction (about 20 mg). GC-ratio of cis/trans isomers was 21:48.

After the reaction was complete according to GC data the reaction mixture was washed with saturated $NH_4Cl$ solution and brine. The methylene chloride solution was dried over $Na_2SO_4$. Concentration gave 13 g of crude product as yellow oil. Purified by column chromatography on silica (200 g, ethyl acetate/hexane 1:20). Only trans isomer was obtained in pure form. The required cis form could not be purified by the technique used. Fractions which were more enriched with required product were combined (200 mg, cis/trans ratio 70:30 according to GC) and used for further transformations.

d) 5-Methoxy-1a,2,3,7b-tetrahydro-1H-cyclopropa[a]naphthalene-1-carboxylic acid

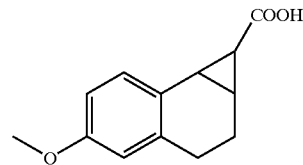

Ethyl 5-methoxy-1a,2,3,7b-tetrahydro-1H-cyclopropa[a]naphthalene-1-5 carboxylate (0.2 g, 0.8 mmol) was dissolved in 2 ml of methanol and the solution of sodium hydroxide (0.2 g, 50 mmol) in 2 ml of water was added to the reaction mixture and stirred at ambient temperature overnight. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over $Na_2SO_4$ and concentrated by rotary evaporation to give 0.15 g of mixture of cis/trans acids as white solid.

e) +/−cis-N-(5-cyano-2-pyridinyl)-N-(5-methoxy-1a, 2,3,7b-tetrahydro-1H-cyclopropa[a]naphthalen-1-yl) urea

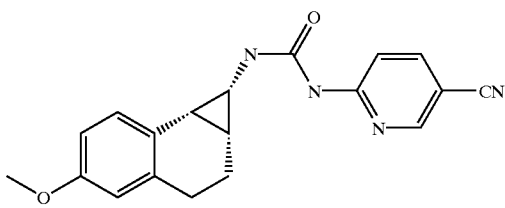

5-Methoxy-1a,2,3,7b-tetrahydro-1H-cyclopropa[a] naphthalene-1-carboxylic acid (150 mg, 0.69 mmol, cis/trans mixture about 70:30) was mixed with toluene (7 ml), triethylamine (1.1 eq), 5-cyano-2-aminopyridine (1.1 eq), DPPA (1.1 eq) and bubbled with argon for about 5 min. The reaction mixture was then heated at stirring at 115° C. for 3 h under argon. The reaction mixture was concentrated by rotary evaporation and purified by column chromatography on silica (100 g, ethylacetate/hexane 1:20). Desired product (+/−cis isomer) was obtained as beige-white powder (80 mg, yield 35%).

$^1$H-NMR (CDCl$_3$): 9.02 (br s,1H), 8.60 (br s, 1H), 7.77 (br s, ~1H), 7.68 (br d, 1H), 7.25 (s, ~1H), 6.82 (dd, 2H), 6.64 (d, 1H), 3.83 (s, 3H), 3.25 (br s,1H), 2.80–2.71 (m, 1H), 2.50–2.42 (m, 1H), 2.24 (t, 1H), 2.18–2.09 (m, 1H), 1.75–1.61 (m, 2H).

EXAMPLE 6

+/−cis-N-(5-cyano-2-pyridinyl)-N-(6-methoxy-1a,2,3, 7b-tetrahydro-1H cyclopropa[a]naphthalen-1-yl)urea a) 7-methoxy-1,2,3,4-tetrahydro-1-naphthalenol

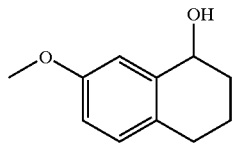

7-Methoxy-3,4-dihydro-1(2H)-naphthalenol was synthesized analogously to Example 5a from 7-methoxy-1,2,3,4-tetrahydro-1-naphthalenone (5 g, 28 mmol), to give about 5 g of crude product (quantitative yield), which was used in the next step without additional purification.

b) 6-methoxy-1,2-dihydronaphthalene

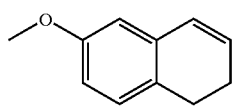

6-Methoxy-1,2-dihydronaphthalene was synthesized analogously to Example 5b from 7-methoxy-1,2,3,4-tetrahydro-1-naphthalenol to give 4.4 g of product brown yellow oil (96% yield from 7-methoxy-1,2,3,4-tetrahydro-1-naphthalenone).

c) Ethyl 6-methoxy-1a,2,3,7b-tetrahydro-1H-cyclopropa[a]naphthalene-1-carboxylate

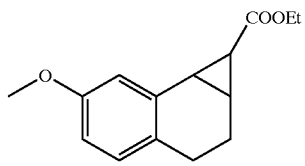

Ethyl 6-methoxy-1a,2,3,7b-tetrahydro-1H-cyclopropa[a] naphthalene-1-carboxylate was synthesized analogously to Example 3 from 6-methoxy-1,2-dihydronaphthalene (4.4 g, 28 mmol) at addition rate 0.7 ml/h to give 9.68 g of crude product as orange-brown oil. Purified by column chromatography on silica (200 g, ethylacetate/hexane 1:10). Three fractions were collected: fraction enriched with cis isomer (75% by GC)—0.16 g, mixed fraction —1.76 g, and fraction contained pure trans isomer—1 g. Total yield 45%.

d) 6-methoxy-1a,2,3,7b-tetrahydro-1H-cyclopropa[a]naphthalene-1-carboxylic acid

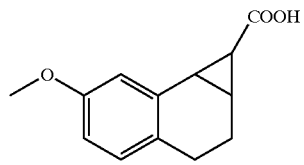

6-Methoxy-1a,2,3,7b-tetrahydro-1H-cyclopropa[a] naphthalene-1-carboxylic acid was synthesized analogously to Example 5d) from ethyl 6-methoxy-1a,2,3,7b-tetrahydro-1H-cyclopropa[a]naphthalene-1-carboxylate (0.16 g, 0.65 mmol) to give 0.1 g of product as white crystals. Yield 71%.

e) +/−cis-N-(5-cyano-2-pyridinyl)-N-(6-methoxy-1a, 2,3,7b-tetrahydro-1H-cyclopropa[a]naphthalen-1-yl) urea.

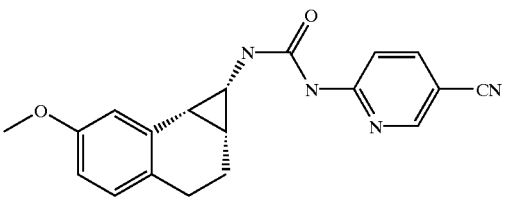

+/−cis-N-(5-cyano-2-pyridinyl)-N-(6-methoxy-1a,2,3, 7b-tetrahydro-1H-cyclopropa[a]naphthalen-1-yl)urea was synthesized analogously to Example 5e from 6-methoxy-1a, 2,3,7b-tetrahydro-1H-cyclopropa[a]naphthalene-1-5 carboxylic acid (0.1 g, 0.46 mmol) to give 0.06 g of product as white crystals. Yield 39%.

$^1$H-NMR (CDCl$_3$): 8.55 (br s, ~1H), 8.13 (br s, 1H), 7.81 (br s, ~1H), 7.69 (br d, 1H), 7.00 (d, 1H), 6.91 (d, 1H), 6.78 (dd, 1H), 6.73 (br s, ~1H), 3.83 (s, 3H), 3.33 (br s, 1H), 2.74–2.66 (m, 1H), 2.50–2.42 (m, 1H), 2.27 (t, 1H), 2.17–2.06 (m, 1H), 1.78–1.67 (m, 2H).

EXAMPLE 7

+/−cis-N-(5-cyano-1a,2,3,7b-tetrahydro-1H-cyclopropa[a]naphthalen-1-yl)-N-(5-cyano-2-pyridinyl)urea a) 7,8-dihydro-2-naphthalenol

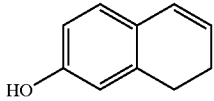

7-Methoxy-1,2-dihydronaphthalene[see.2] (6.4 g, 40 mmol) was dissolved in abs. DMF and bubbled with argon sodium ethylthiolate (2.5 eq) was added and the reaction mixture was heated at stirring at 160° C. for about 4 h. Reaction was monitored by GC. Reaction mixture was diluted with water, acidified with 3M HCl and extracted into ethylacetate. Organic extract was washed with water and brine, dried over $Na_2SO_4$ and concentrated by rotary evaporation. Purification by column chromatography on silica (200 g, ethylacetate/hexane) gave 5.36 g of desired phenol. Yield 92%.

b) 7,8-dihydro-2-naphthalenyl trifluoromethanesulfonate

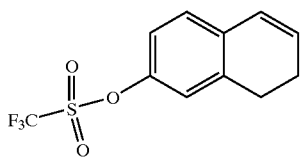

7,8-Dihydro-2-naphthalenol (5.3 g, 37 mmol) was mixed with triethylamine (6.2 ml, 44 mmol) in abs. methylenechloride and cooled under nitrogen in the ice/brine bath. Triflic anhydride (7.4 ml, 44 mmol) was added to the stirred solution through syringe during 10 min. The temperature was allowed to rise slowly up to room temperature. The reaction mixture was then washed with water and brine and dried over $Na_2SO_4$. The crude product was purified by column chromatography on silica. 9 g of brown liquid was obtained. Yield 88%.

c) Ethyl 5-{[(trifluoromethyl)sulfonyl]oxy}-1a,2,3,7b-tetrahydro-1H-cyclopropa[a]naphthalene-1-carboxylate

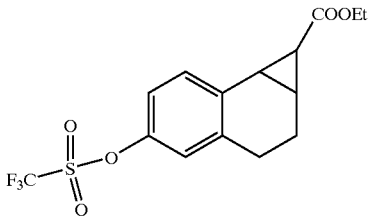

Ethyl 5-{[(trifluoromethyl)sulfonyl]oxy}-1a,2,3,7b-tetrahydro-1H-cyclopropa[a]naphthalene-1-carboxylate was synthesized analogously to Example 5c from 7,8-dihydro-2-naphthalenyl trifluoromethanesulfonate (9 g, 32 mmol) at addition rate 1 ml/h to give 13 g of crude product as orange-brown oil. Purified by column chromatography on silica (200 g, ethylacetate/hexane 1:15). Fraction enriched with cis isomer (80% by GC)—0.64 g was collected and used for further transformations.

d) Ethyl 5-cyano-1a,2,3,7b-tetrahydro-1H-cyclopropa[a]naphthalene-1-carboxylate

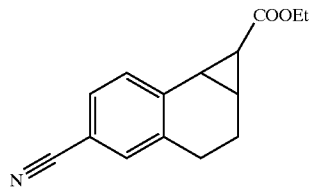

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with $Zn(CN)_2$ (0.82 mmol) and $Pd(Ph_3P)_4$ (56 mg, 10 mol %) in DMF (4 ml), bubbled with argon for 5 min and heated at stirring in a closed vial for 14 h at 100° C. Reaction was monitored by GC. The reaction mixture was concentrated by rotary evaporation, mixed with saturated $NH_4Cl$ and extracted into ethylacetate (3×15 ml). Organic extract was washed with water and brine, dried under $Na_2SO_4$. Concentration gave 0.12 g of product as an oil (yield 90%).

d) 5-cyano-1a,2,3,7b-tetrahydro-1H-cyclopropa[a]naphthalene-1-carboxylic acid

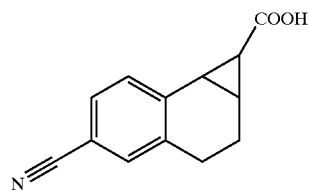

5-Cyano-1a,2,3,7b-tetrahydro-1H-cyclopropa[a]naphthalene-1-carboxylic acid was synthesized analogously to Example 5d from ethyl 5-cyano-1a,2,3,7b-tetrahydro-1H-cyclopropa[a]naphthalene-1-carboxylate (0.12 g, 0.5 mmol) to give 0.1 g of product as white crystals. Yield 94%.

e) +/−cis-N-(5-cyano-1a,2,3,7b-tetrahydro-1H-cyclopropa[a]naphthalen-1-yl)-N-(5-cyano-2-pyridinyl)urea

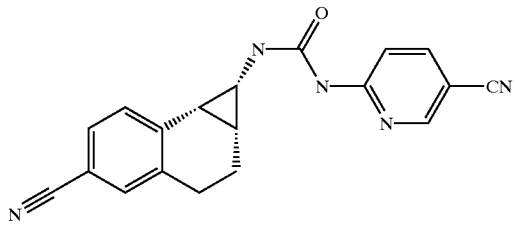

+/−cis-N-(5-cyano-1a,2,3,7b-tetrahydro-1H-cyclopropa[a]naphthalen-1-yl)-N-(5-cyano-2-pyridinyl)urea was synthesized analogously to Example 5e from 5-cyano-1a,2,3,7b-tetrahydro-1H-cyclopropa[a]naphthalene-1-carboxylic acid (0.1 g, 0.46 mmol) to give 45 mg of product (precipitated from the reaction mixture and washed with small amount of ethanol) as grey powder. Yield 29%.

$^1$H-NMR (DMSO-$d_6$): 9.70 (br s, 1H), 8.32 (br s, 1H), 8.03 (dd, 1H), 7.46–7.63 (m, 4H), 7.32 (br s, 1H), 3.18–3.10 (m, 2H), 2.76–2.65(m, 1H), 2.62–2.51 (m, 1H), 2.34 (t, 1H), 2.01–1.80 (br m, 2H), 1.78–1.69 (br m, 1H).

EXAMPLE 8

+/−cis-N-(5-cyano-2-pyridinyl)-N-(5-ethynyl-1a,2,3,7b-tetrahydro-1H-cyclopropa[a]naphthalen-1-yl)urea a) Ethyl 5-[(trimethylsilyl)ethynyl]-1a,2,3,7b-tetrahydro-1H-cyclopropa[a]naphthalene-1-carboxylate

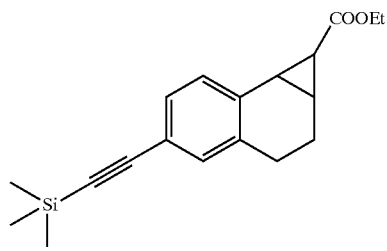

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with trimethylsylilacetylene (0.2 ml, 1.37 mmol), DPP (35 mg, 10 mol %), Pd(dba)$_2$ (30 mg, 10 mol %) and CuI (3 mg) in Et$_3$N (2.5 ml), bubbled with argon for 5 min and heated at stirring in a closed vial for 14 h at 95° C. Reaction was monitored by GC. The reaction mixture was concentrated by rotary evaporation, mixed with saturated NH$_4$Cl and extracted into ethylacetate (3×15 ml). Organic extract was washed with water and brine, dried under Na$_2$SO$_4$. Concentration gave 0.15 g of product as an oil (yield 87%).

b) 5-Ethynyl-1a,2,3,7b-tetrahydro-1H-cyclopropa[a]naphthalene-1-carboxylic acid

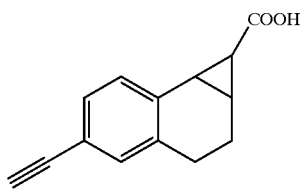

Ethyl 5-[(trimethylsilyl)ethynyl]-1a,2,3,7b-tetrahydro-1H-cyclopropa[a]naphthalene-1-carboxylate (0.2 g, 0.64 mmol) was dissolved in 4ml of methanol and the solution of sodium hydroxide (0.05 g, 1.2 mmol) in 2 ml of water was added to the reaction mixture and stirred at heating at 65° C. for 6 h. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over Na$_2$SO$_4$ and concentrated by rotary evaporation to give 0.12 g of mixture of cis/trans acids (85:15) as white solid. Yield 88%.

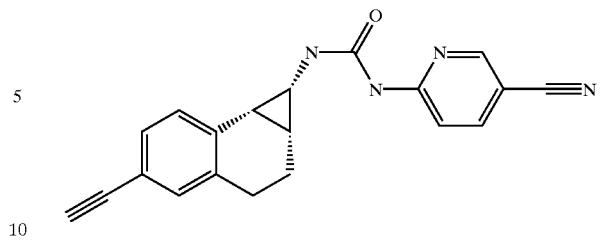

+/−cis-N-(5-cyano-2-pyridinyl)-N-(5-ethynyl-1a,2,3,7b-tetrahydro-1H-cyclopropa[a]naphthalen-1-yl)urea was synthesized analogously to Example 5e from 5-ethynyl-1a,2,3,7b-tetrahydro-1H-cyclopropa[a]naphthalene-1-carboxylic acid (60 mg, 0.29 mmol) to give 15 mg of product (precipitated from the reaction mixture and washed with small amount of ethanol) as grey powder. Yield 16%.

$^1$H-NMR (DMSO-d$_6$): 9.74 (br s,1H), 8.20 (br s,1H), 8.00 (br d, 1H), 7.47 (br d, 1H), 7.28 (br m, 3H), 7.19 (br s, 1H), 4.09 (s, 1H), 3.29 (br s, ~1H +overlapped H$_2$O signal), 3.08 (br m, 1H), 2.58–2.69 (br m, 1H), 2.23 (br t, 1H), 2.00–1.85 (br m, 1H), 1.80–1.55 (br m, 2H).

EXAMPLE 9

+/−cis-N-(5-bromo-2-pyridinyl)-N-(5-ethynyl-1a,2,3,7b-tetrahydro-1H-cyclopropa[a]naphthalen-1-yl)urea

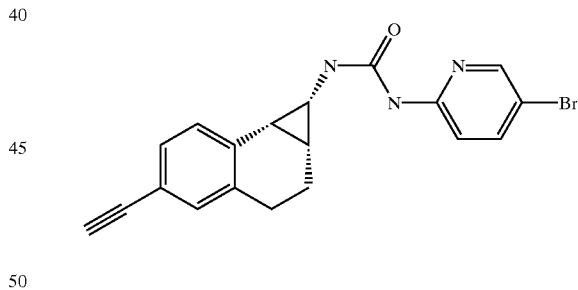

±/−cis-N-(5-bromo-2-pyridinyl)-N-(5-ethynyl-1a,2,3,7b-tetrahydro-1H-cyclopropa[a]naphthalen-1-yl)urea was synthesized analogously to Example 5e from 5-ethynyl-1a,2,3,7b-tetrahydro-1H-cyclopropa[a]naphthalene-1-carboxylic acid (40 mg, 0.19 mmol) and 2-amino-5-bromopyridine (1.1 eq) to give 10 mg of product (precipitated from the reaction mixture and washed with small amount of ethanol) as brownish powder. Yield 14%.

$^1$H-NMR (CDCl$_3$): 8.60 (br s, ~1H), 7.60 (m, 3H), 7.35 (dd, 1H), 7.30 (d, 1H), 7.22 (m, 1H), 6.55 (br s,1H), 3.30 (m, 1H), 3.07 (s, ~1H), 2.78–2.67 (m, 1H), 2.57–2.51 (m, 1H), 2.30 (t, 1H), 2.17–2.09 (m, 1H), 1.85–1.70 (m, 2H).

EXAMPLE 10

+/−cis-N-(5-ethynyl-1a,2,3,7b-tetrahydro-1H-cyclopropa[a]naphthalen-1-yl)-N-(5-phenoxy-2-pyridinyl)urea

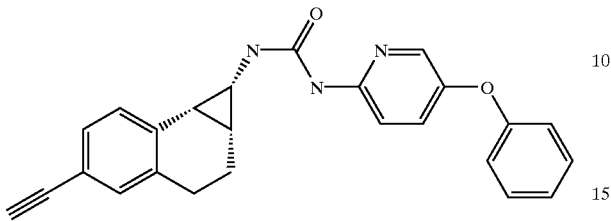

+/−cis-N-(5-ethynyl-1a,2,3,7b-tetrahydro-1H-cyclopropa[a]naphthalen-1-yl)-N-(5-phenoxy-2-pyridinyl)urea was synthesized analogously to Example 5e from 5-ethynyl-1a,2,3,7b-tetrahydro-1H-cyclopropa[a]naphthalene-1-carboxylic acid (40 mg, 0.19 mmol) and 2-amino-5-phenoxypyridine (1.1 eq) to give 13 mg of product (separated by chromatography) as slightly brownish powder. Yield 17%.

$^1$H-NMR (CDCl$_3$): 8.75 (br s, 1H), 7.79 (s, 1H), 7.42 (br s, 1H), 7.33 (m, 2H), 7.29 (br s, 2H), 7.23 (dd, 1H), 7.18 (br s, 1H), 7.10 (m, 1H), 6.94 (m, 2H), 6.65 (br s, 1H), 3.30 (m, 1H), 2.93 (s, ~1H), 2.77–2.67 (m, 1H), 2.60–2.51 (m, 1H), 1.91–1.81 (m, 1H), 1.79–1.70 (m, 1H).

EXAMPLE 11

+/−cis-N-[5-(diethylamino)-2-pyridinyl]-N-(5-ethynyl-1a,2,3,7b-tetrahydro-1H-cyclopropa[a]naphthalen-1-yl)urea

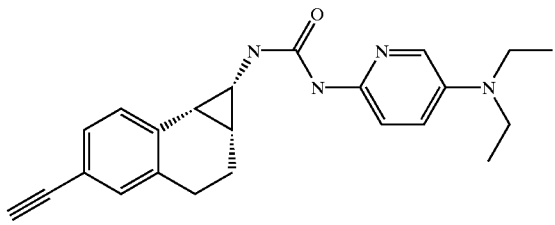

+/−cis-N-[5-(diethylamino)-2-pyridinyl]-N-(5-ethynyl-1a,2,3,7b-tetrahydro-1H-cyclopropa[a]naphthalen-1-yl)urea was synthesized analogously to Example 5e from 5-ethynyl-1a,2,3,7b-tetrahydro-1H-cyclopropa[a]naphthalene-1-carboxylic acid (40 mg, 0.19 mmol) and 2-amino-5-diethylaminopyridine (1.1 eq) to give 4 mg of product (separated by chromatography) as slightly brownish powder. Yield 6%.

$^1$H-NMR (CDCl$_3$): 8.95 (br s, ~1H), 7.38–7.31 (m, 2H), 7.24 (br s, 1H), 6.93–6.91 (m, 2H), 6.6 (br s, 1H), 6.4 (br s, 1H), 3.36 (br m, 1H), 3.23 (q, 4H), 3.00 (s, 1H), 2.71 (m, 1H), 2.58 (m, 1H), 2.26 (t, 1H), 2.15–2.03 (m, 1H), 1.91–1.82 (m, 1H), 1.77–1.68 (m, 1H), 1.10 (t, 6H).

EXAMPLE 12 anti-+/−cis-N-(5-cyano-2-pyridinyl)-N-(4,7-difluoro-3-methyl-1a,2,3,7b-tetrahydro-1H-cyclopropa[a]naphthalen-1-yl) urea a) 5,8-difluoro-4-methyl-3,4-dihydro-1(2H)-naphthalenone

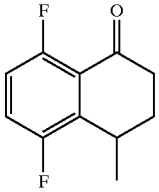

1,4-Difluorobenzene (22 ml, 210 mmol) was mixed with □-valerolactone (4 ml, 42 mmol) and AlCl$_3$ (28 g, 210 mmol) was added by portions to the stirred reaction mixture. The reaction mixture was then refluxed at stirring for 16 h (oil bath 110° C.). The reaction mixture was cooled down (ice/brine bath) and ice/conc. HCl was added and stirred until homogeneous mixture was obtained. The reaction mixture was then extracted into methylene chloride, washed with water (4×10 ml) and sodium bicarbonate solution (3×100 ml). The organic extract was dried over Na$_2$SO$_4$. Concentration by rotary evaporation gave 6.7 g of product as yellow powder. Yield 81%.

b) 5,8-difluoro-4-methyl-1,2,3,4-tetrahydro-1-naphthalenol

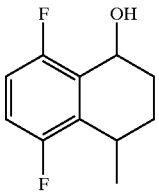

5,8-Difluoro-4-methyl-1,2,3,4-tetrahydro-1-naphthalenol was synthesized analogously to Example 5a from 5,8-difluoro-4-methyl-3,4-dihydro-1(2H)-naphthalenone to give 1.8 g of crude product, which was used in the next step without additional purification.

c) 5,8-difluoro-1-methyl-1,2-dihydronaphthalene

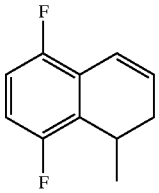

5,8-Difluoro-1-methyl-1,2-dihydronaphthalene was synthesized analogously to Example 5b from 5,8-difluoro-4-methyl-1,2,3,4-tetrahydro-1-naphthalenol (1.8 g, 9.1 mmol) to give 1.5 g of product as brown yellow oil (90% yield from 5,8-difluoro-4-methyl-1,2,3,4-tetrahydro-1-naphthalenone).

d) Ethyl 4,7-difluoro-3-methyl-1a,2,3,7b-tetrahydro-1H-cyclopropa[a]naphthalene-1-carboxylate

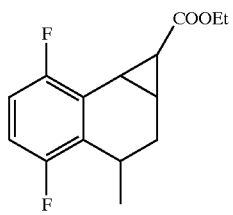

Ethyl 4,7-difluoro-3-methyl-1a,2,3,7b-tetrahydro-1H-cyclopropa[a]naphthalene-1-carboxylate was synthesized analogously to Example 5c from 5,8-difluoro-1-methyl-1,2-dihydronaphthalene (3.5 g, 19 mmol) at addition rate 0.5 ml/h to give crude product as yellow-brown oil. Purified by column chromatography on silica (200 g, ethylacetate/hexane 1:15) to give 5.2 g of the mixture of diastereomeric esters together with dimers of EDA as colourless oil (GC ratio: anti-45%; 40% /trans:cis/, syn-11%; 2.3% /trans:cis).

e) +/−anti-cis-4,7-difluoro-3-methyl-1a,2,3,7b-tetrahydro-1H-cyclopropa[a]naphthalene-1-carboxylic acid

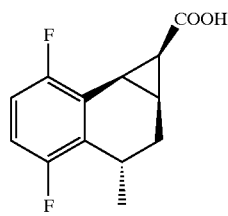

Ethyl 4,7-difluoro-1a,2,3,7b-tetrahydro-1H-cyclopropa[a]naphthalene-1-carboxylate (5.25 g, 20 mmol, ~50:50 mixture of cis and trans isomers) was dissolved in 2.5 ml of methanol and the solution of sodium hydroxide (0.4 g, 10 mmol) in 2.5 ml of water was added to the reaction mixture and stirred at ambient temperature overnight. The reaction mixture was extracted into hexane (3×30 ml). The combined extracts were washed with water and brine, dried over $Na_2SO_4$ and concentrated by rotary evaporation to give 1.12 g of cis esters as colourless oil (mixture of ethyl and methyl esters—94% according to GC). The mixture obtained was dissolved in 1.5 ml of methanol and the solution of sodium hydroxide (0.2 g, 5 mmol) in 1.5 ml of water was added to the reaction mixture and stirred at 95° C. for 40 min. The reaction mixture was acidified with excess of 3M HCl solution (pH=1), and extracted into ethylacetate (3×15 ml). The combined extracts were washed with water and brine, dried over $Na_2SO_4$ and concentrated by rotary evaporation to give 0.93 g anti-+/−cis acid as slightly orange crystals. Yield 20% (appr. quantitative if calculated for starting cis isomer).

f) anti-+/−cis-N-(5-cyano-2-pyridinyl)-N-(4,7-difluoro-3-methyl-1a,2,3,7b-tetrahydro-1H-cyclopropa[a]naphthalen-1-yl)urea

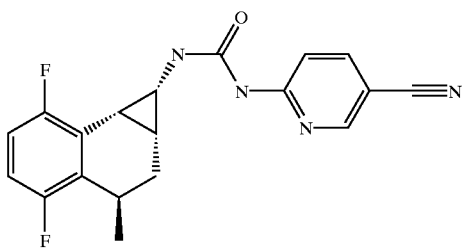

anti-+/−cis-N-(5-Cyano-2-pyridinyl)-N-(4,7-difluoro-3-methyl-1a,2,3,7b-tetrahydro-1H-cyclopropa[a]naphthalen-1-yl)urea was synthesized analogously to Example 5e from +/−anti-cis-4,7-difluoro-3-methyl-1a,2,3,7b-tetrahydro-1H-cyclopropa[a]naphthalene-1-carboxylic acid (200 mg, 0.8 mmol) to give 90 mg of product (precipitated from the reaction mixture and washed with small amount of ethanol) as white powder. Yield 30%. Antiplanar orientation of external 3-methyl group in cyclohexyl ring was proved by 2D NMR experiments.

$^1$H-NMR (DMSO-d6): 9.86 (s, 1H), 8.19 (d, 1H), 8.05 (dd, 1H), 7.48 (d, 1H), 7.32 (b rs, 1H), 7.11–7.32 (m, 2H), 3.25 (ddd, 1H), 3.09 (br m, 1H), 2.21 (t, 1H), 2.02 (ddd, 1H), 1.65 (m, 1H), 1.35 (m, 2H), 1.22 (d, 3H).

EXAMPLE 13 anti-+/−cis-N-(5-cyano-2-pyridinyl)-N-(2,5-difluoro-6-methyl-1,1a6,6a-tetrahydrocyclopropa[a]inden-1-yl)urea a) 4,7-difluoro-3-methyl-1-indanone

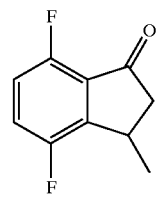

4,7-Difluoro-3-methyl-1-indanone was synthesized analogously to Example 12a from □-butyrolactone (4 ml, 52 mmol) to give 7.19 g of yellow powder (85:15 mixture of corresponding indanone and tertralone according to GC). The product was purified by column chromatography on silica (200 g, ethylacetate/hexane) to give 3.7 g (40% yield) of pure product together with mixed fraction and fraction containing pure tetralone.

b) 4,7-difluoro-3-methyl-1-indanol

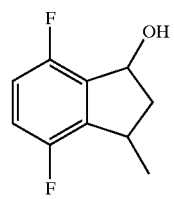

4,7-Difluoro-3-methyl-1-indanol was synthesized analogously to Example 5 from 4,7-difluoro-3-methyl-1-indanone (3.7 g, 20 mmol), to give about 3.75 g of crude product (quantitative yield), which was used in the next step without additional purification.

c) 4,7-Difluoro-1-methyl-1H-indene

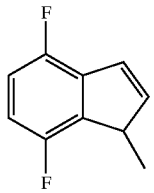

4,7-Difluoro-1-methyl-1H-indene was synthesized analogously to Example 2 from 4,7-difluoro-3-methyl-1-indanol (3.75 g, 9.1 mmol) to give 2.36 g of product as beige liquid (70% yield).

d) Ethyl 2,5-difluoro-6-methyl-1,1a,6,6a-tetrahydrocyclopropa[a]indene-1-carboxylate

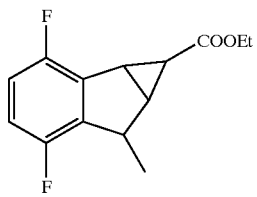

Ethyl 2,5-difluoro-6-methyl-1,1a,6,6a-tetrahydrocyclopropa[a]indene-1-carboxylate was synthesized analogously to Example 5c from 4,7-difluoro-1-methyl-1H-indene (1.32 g, 7.9 mmol) at addition rate 0.4 ml/h to give crude product as yellow-brown oil. Purified by column chromatography on silica (100 g, ethylacetate/hexane 1:15) to give 0.61 g of the mixture of diastereomeric esters cis- and trans-esters as colourless oil (cis/trans ratio: 84:16 according to NMR). Yield 30%.

e) anti-+/−cis-2,5-difluoro-6-methyl1,1a,6,6a-tetrahydrocyclopropa[a]indene-1-carboxylic acid

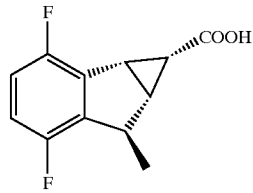

anti-+/−cis-2,5-Difluoro-6-methyl-1,1a,6,6a-tetrahydrocyclopropa[a]indene-1-carboxylic acid was synthesized analogously to Example 34 from ethyl 2,5-difluoro-6-methyl-1,1a,6,6a-tetrahydrocyclopropa[a]indene-1-carboxylate (0.61 g, 2.4 mmol) by stepwise hydrolysis first with 20 mol. % of NaOH and then with the excess of NaOH at heating to give 380 mg of product as white crystals. Yield 70% (appr. quantitative if calculated for starting cis isomer).

f) 38. anti-+/−cis-N-(5-cyano-2-pyridinyl)-N-(2,5-difluoro-6-methyl-1,1a,6,6a-tetrahydrocyclopropa[a]inden-1-yl)urea

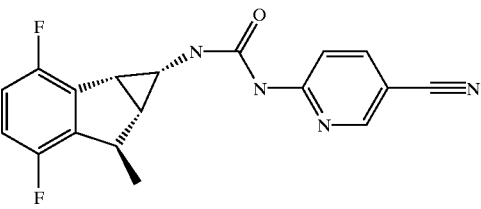

anti-+/+cis-N-(5-cyano-2-pyridinyl)-N-(2,5-difluoro-6-methyl-1,1a,6,6a-tetrahydrocyclopropa[a]inden-1-yl)urea urea was synthesized analogously to Example 5 from anti-+/−cis-2,5-difluoro-6-methyl-1,1a,6,6a-tetrahydrocyclopropa [a]indene-1-carboxylic acid (100 mg, 0.44 mmol) to give 30 mg of product (precipitated from the reaction mixture and washed with small amount of ethanol) as white powder. Yield 20%.

$^1$H-NMR (DMSO-$d_6$): 9.60 (s, 1H), 8.33 (br s, 1H), 8.01 (dd, 1H), 7.44 (d, 1H), 7.32 (br s,1H), 7.05–6.91 (m, 2H), 3.31–2.90 (m, 2H+overlapped H$_2$O signal), 2.93 (br t,1H), 1.95 (br t, 1H), 1.28 (d, 3H).

EXAMPLE 14 anti-+/−cis-N-(2,5-difluoro-6-methyl1,1a,6,6a-tetrahydrocyclopropa[a]inden-1-yl)-N-(5-phenoxy-2-pyridinyl)urea

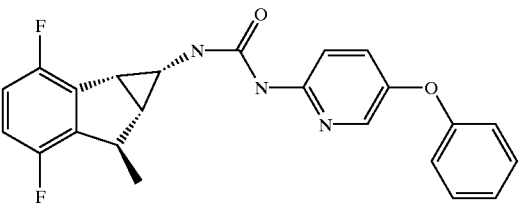

anti-+/−cis-N-(2,5-difluoro-6-methyl-1,1a,6,6a-tetrahydrocyclopropa[a]inden-1-yl)-N-(5-phenoxy-2-pyridinyl)urea was synthesized analogously to Example 5e from anti-+/−cis-2,5-difluoro-6-methyl-1,1 a,6,6a-tetrahydrocyclopropa[a]indene-1-carboxylic acid (50 mg, 0.22 mmol) to give 33 mg of product as white powder (purified by column chromatography on prepacked Biotage/silica/column, ethylacetate/hexane 1:1). Yield 36%.

$^1$H-NMR (CDCl$_3$): 8.80 (br s, 1H), 8.15 (s, 1H), 7.44 (d, 1H), 7.36 (m, 2H), 7.23 (dd, 1H), 7.13 (m, 1H), 6.93 (m, 1H), 6.92 (m, 1H), 6.78 (m, 1H), 6.72–6.62 (m, 2H), 3.56 (m, 1H), 3.31 (m, 1H), 2.97 (br t, 1H), 1.36 (d, 3H).

EXAMPLE 15 anti-+/−cis-N-[5-(diethylamino)-2-pyridinyl]-N-(2,5-difluoro-6-methyl1-1,1a,6,6a-tetrahydrocyclopropa[a]inden-1-yl)urea

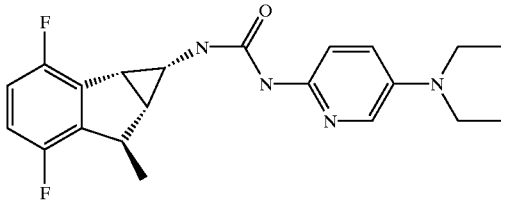

anti-+/−cis-N-[5-(diethylamino)-2-pyridinyl]-N-(2,5-difluoro-6-methyl-1,1a,6,6a-tetrahydrocyclopropa[a]inden-1-yl)urea was synthesized analogously to Example 5 from anti-+/−cis-2,5-difluoro-6-methyl-1,1a,6,6a-tetrahydrocyclopropa[a]indene-1-carboxylic acid (50 mg, 0.22 mmol) to give 25 mg of product as beige powder (purified by column chromatography on prepacked Biotage/silica/column, ethylacetate/hexane 1:1). Yield 29%.

$^1$H-NMR (CDCl$_3$): 8.95 (br s, 1H), 7.84 (d, 1H), 7.15 (br d, 1H), 6.93 (dd, 2H), 6.82 (m, 1H), 6.72 (m, 1H), 6.45 (br d, 1H), 3.59 (dd, 1H), 3.38–3.27 (m, 1H), 3.22 (q, 4H), 2.97 (m, 1H), 1.38 (d, 3H), 1.11 (t, 6H).

EXAMPLE 16 anti-+/−cis-N-(5-cyano-2-pyridinyl)-N-(4,7-difluoro-1a2,3,7b-tetrahydro-1H-cyclopropa[a]naphthalen-1-yl)urea a) 5,8-difluoro-3,4-dihydro-1(2H)-naphthalenone

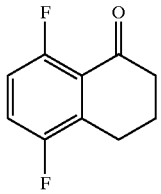

5,8-Difluoro-3,4-dihydro-1(2H)-naphthalenone was synthesized together with 4,7-difluoro-3-methyl-1-indanone according to procedure described in Example 13a. Separated by column chromatography on silica. 0.77 g of pure product was obtained yield 8%.

b) 5,8-difluoro-1,2,3,4-tetrahydro-1-naphthalenol

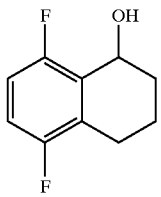

5,8-Difluoro-1,2,3,4-tetrahydro-1-naphthalenol was synthesized analogously to Example 5from a 5,8-difluoro-3,4-dihydro-1(2H)-naphthalenone (0.77 g, (4.2 mmol), to give crude product (quantitative yield), which was used in the next step without additional purification.

c) 5,8-difluoro-1,2-dihydronaphthalene

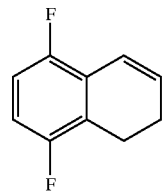

5,8-Difluoro-1,2-dihydronaphthalene was synthesized analogously to Example 5b from 5,8-difluoro-1,2,3,4-tetrahydro-1-naphthalenol to give 0.67 g of crude product as brownish liquid (90% yield from 5,8-difluoro-3,4-dihydro-1(2H)-naphthalenone).

Additional amount of product was also obtained from the mixture of 5,8-difluoro-3,4-dihydro-1(2H)-naphthalenone and 4,7-difluoro-3-methyl-1-indanone by reduction followed by dehydration. The mixture of corresponding indene and naphthalene is easy to separate by column chromatography on silica (ethyl acetate/hexane 1:20).

d) ethyl 4,7-difluoro-1a,2,3,7b-tetrahydro-1H-cyclopropa[a]naphthalene-1-carboxylate

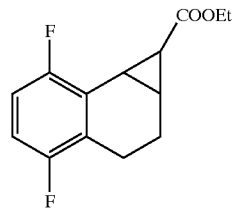

Ethyl 4,7-difluoro-1a,2,3,7b-tetrahydro-1H-cyclopropa[a]naphthalene-1-carboxylate was synthesized analogously to Example 5c from 5,8-difluoro-1,2-dihydronapthalene (0.7 g, 4.2 mmol) at addition rate 0.4 ml/h to give crude product as yellow-brown oil. Purified by column chromatography on silica (100 g, ethylacetate/hexane 1:15) to give 0.45 g of the mixture of cis- and trans-esters as colourless oil (cis/trans ratio: 33:67 according to GC). 4,7-difluoro-1a,2,3,7b-tetrahydro-1H-cyclopropa[a]naphthalene-1-carboxylic acid e) 4,7-Difluoro-1a,2,3,7b-tetrahydro-1H-cyclopropa[a]naphthalene-1-carboxylic acid

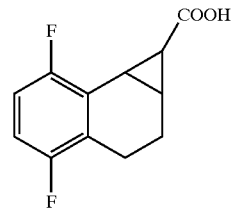

4,7-Difluoro-1a,2,3,7b-tetrahydro-1H-cyclopropa[a]naphthalene-1-carboxylic acid was synthesized analogously to Example 12e from ethyl 4,7-difluoro-1a,2,3,7b-tetrahydro-1H-cyclopropa[a]naphthalene-1-carboxylate (0.45 g, 1.8 mmol) by stepwise hydrolysis first with excess of NaOH at r.t. and then with the excess of NaOH at heating (60° C., 1.5 h) to give 80 mg of product as white crystals (cis/trans ratio 78:22 according to HPLC).

f) anti-+/−cis-N-(5-cyano-2-pyridinyl)-N-(4,7-difluoro-1a,2,3,7b-tetrahydro-1H-cyclopropa[a]naphthalen-1-yl)urea

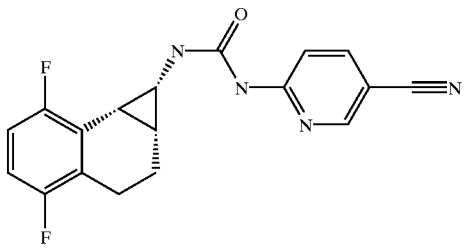

anti-+/−cis-N-(5-cyano-2-pyridinyl)-N-(4,7-difluoro-1a,2,3,7b-tetrahydro-1H-cyclopropa[a]naphthalen-1-yl)urea was synthesized analogously to Example 5 from 4,7-difluoro-1a,2,3,7b-tetrahydro-1H-cyclopropa[a]naphthalene-1-carboxylic acid (80 mg, 0.36 mmol) to give 33 mg of product (precipitated from the reaction mixture and washed with small amount of ethanol) as white powder. Yield 27%.

$^1$H-NMR (DMSO-$d_6$): 9.73 (s, 1H), 8.29 (d, 1H), 8.04 (dd, 1H), 7.53 (d, 1H), 7.32 (br s, 1H), 7.14–7.02 (m, 2H), 3.17 (ddd, 1H), 2.69–2.59 (m, 1H), 2.52–2.42 (m, ~1H+ overlapped DMSO signal), 2.30 (t, 1H), 1.99 (m, 1H), 1.71 (m, 2H).

EXAMPLE 17

(±)-cis-1-(5-cyano-2-pyridinyl)-3-(4-bromo-1,1a,6,6a-tetrahydro-cyclopropa[a]inden-1-yl)-urea a) 6-Bromoindene

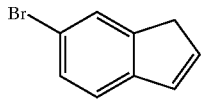

This compound was prepared analogously to Examples 5a and 5b from 5-bromo-1-indanone (4.0 g, 18.8 mmol) to give 2.4 g (65%) of 6-bromoindene.

b) (±)-cis-Ethyl 4-bromo-1,1a,6,6a-tetrahydrocyclopropa[a]indene-1-carboxylate

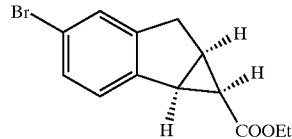

This compound was prepared analogously to Example 5c from 6-bromoindene (1.95 g, 10 mmol). Purification on silica gel starting with hexanes followed by hexanes with 2% diethyl ether and finally hexanes with 5% diethyl ether afforded 670 mg (24%) of the cis-ester.

c) (±)-cis-4-Bromo1,1a,6,6a-tetrahydrocyclopropa[a]indene-1-carboxylic acid

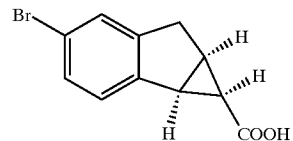

This acid was synthesized analogously to Example 5d starting with 330 mg (1.77 mmol) of the compound from Example 17b to give 232 mg (79%) of (±)-cis-4-Bromo-1,1a,6,6a-tetrahydrocyclopropa[a]indene-1-carboxylic acid.

d) (±)-cis-1-(5-cyano-2-pyridinyl)-3-(4-bromo-1,1a,6,6a-tetrahydro-cyclopropa[a]inden-1-yl)-urea

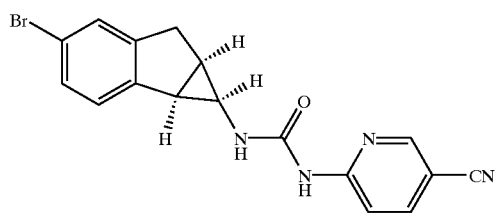

The titled product was prepared analogously to Example 5e from (±)-cis-4-bromo1,1a,6,6a-tetrahydrocyclopropa[a]indene-1-carboxylic acid (79 mg, 0.31 mmol) to give 26 mg (23%) of (±)-cis-1-(5-cyano-2-pyridinyl)-3-(4-bromo-1,1a,6,6a-tetrahydrocyclopropa[a]inden-1-yl)-urea. The compound was pure on HPLC using a C-18 column eluting with 55% acetonitrile and 45% water and gave on LC/MS the two most abundant peaks at m/z 368.9 and 370.9 which correspond to a bromo containing M+1.

EXAMPLE 18

(±)-cis-1-(5-cyano-2-pyridinyl)-3-(4-cyano-1,1a,6,6a-tetrahydro-cyclopropa[a]inden-1-yl)-urea a) (±)-cis-Ethyl 4-cyano-1,1a,6,6a-tetrahydrocyclopropa[a]indene-1-carboxylate

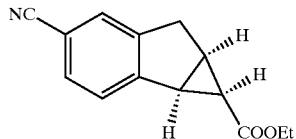

This compound was prepared analogously to Example 7d from (±)-cis-ethyl 4-bromo-1,1a,6,6a-tetrahydrocyclopropa[a]indene-1-carboxylate (200 mg, 0.7 mmol) to give, after purification on silica gel using hexanes with 10% ethyl acetate as the eluent, 73 mg (46%) of (±)-cis-ethyl 4-cyano-1,1a,6,6a-tetrahydrocyclopropa[a]indene-1-carboxylate.

b) (±)-cis-4-Cyano1,1a, 6,6a-tetrahydrocyclopropa[a]indene-1-carboxylic acid

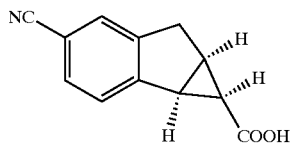

This acid was synthesized analogously to Example 5d starting with 73 mg (0.32 mmol) of the compound from Example 18a to give 59 mg (95%) of (±)-cis-4-cyano1,1a, 6,6a-tetrahydrocyclopropa[a]indene-1-carboxylic acid.

c) (±)-cis-1-(5-cyano-2-pyridinyl)-3-(4-cyano-1,1a, 6,6a-tetrahydro-cyclopropa[a]inden-1-yl)-urea

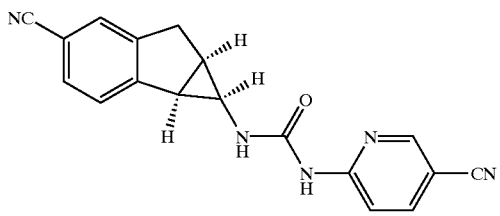

The titled product was prepared analogously to Example 5e from (±)-cis-4-cyano-1,1a,6,6a-tetrahydrocyclopropa[a]indene-1-carboxylic acid (68 mg, 0.30 mmol) to give 15 mg (16%) of (±)-cis-1-(5-cyano-2-pyridinyl)-3-(4-cyano-1,1a, 6,6a-tetrahydrocyclopropa[a]inden-1-yl)-urea. The compound was pure on HPLC using a C-18 column eluting with 55% acetonitrile and 45% water and gave on LC/MS a correct M+1 peak at m/z 316.0

EXAMPLE 19

(±)-cis-1-(5-chloro-2-pyridinyl)-3-(2,5-difluoro-1,1a, 6,6a-tetrahydro-cyclopropa[a]inden-1-yl)-urea a) 4,7-Difluoro-1-indanone

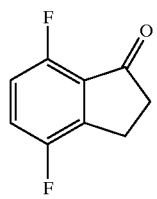

2,5-Difluorocinnamic acid (5.0 g, 27.2 mmol) was dissolved in 25 ml of ethanol and a catalytic amount of 10% Pd on carbon was added. The reaction mixture was hydrogenated at normal pressure for a period of 3 hrs. Filtration through celite and evaporation of the solvent afforded crude 3-(2,5-difluorophenyl)-propionic acid. This acid was dissolved in 75 ml of toluene and 5 ml of thionyl chloride was added. The reaction mixture was heated at +110° C. for a period of 2 hrs. Evaporation of the solvent afforded crude 3-(2,5-difluorophenyl)-propionyl chloride, which was dissolved in 25 ml of carbon disulfide and added drop wise to a suspension of 4 g of aluminium chloride in 100 ml of carbon disulfide. The reaction mixture was refluxed for 2 hrs and gave after work up and re-crystallization from ethanol 975 mg (22%) of 4,7-difluoro-1-indanone.

b) 4,7-Difluoroindene

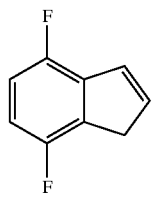

This compound was prepared analogously to Examples 5a and 5b from 4,7-difluoro-1-indanone (975 mg, 5.8 mmol) to give 475 mg (54%) of 4,7-difluoroindene.

c) (±)-cis-Ethyl 2,5-difluoro-1,1a,6,6a-tetrahydrocyclopropa[a]indene-1-carboxylate

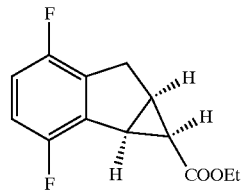

This compound was prepared analogously to Example 5c from 4,7-difluoroindene (475 mg, 3.13 mmol). Purification on silica gel starting with hexanes followed by hexanes with 2% diethyl ether and finally hexanes with 5% diethyl ether afforded 205 mg of the cis-ester contaminated with 22% of the trans-ester.

d) (±)-cis-2,5-Difluoro-1,1a,6,6a-tetrahydrocyclopropa[a]indene-1-carboxylic acid

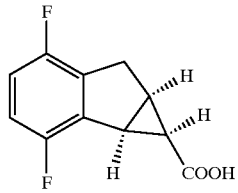

This acid was synthesized analogously to Example 5d starting with 205 mg cis-ester from Example 19c to give 120 mg of (±)-cis-2,5-difluoro-1,1a,6,6a-tetrahydrocyclopropa[a]indene-1-carboxylic acid containing a minor fraction of the corresponding trans-acid.

e) (±)-cis-1-(5-chloro-2-pyridinyl)-3-(2,5-difluoro-1, 1a,6,6a-tetrahydro-cyclopropa[a]inden-1-yl)-urea

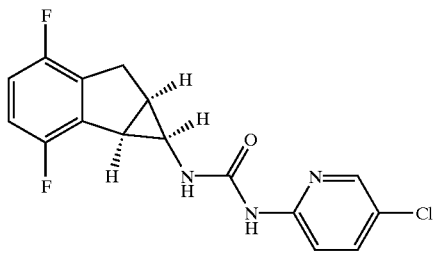

This final compound was prepared analogously to Example 5e from (±)-cis-2,5-difluoro-1,1a,6,6a-tetrahydrocyclopropa[a]indene-1-carboxylic acid (60 mg, 0.28 mmol) and 2-amino-5-chloropyridine (65 mg, 0.5 mmol) to give, after purification on silica gel (ethyl acetate and hexanes 2:1), 27 mg (29%) of the titled compound.

$^1$H-NMR (CDCl$_3$): 8.7 (broad s, 1H), 8.15 (s, 1H), 7.65 (s, 1H), 7.50 (dd, 1H), 6.90–6.78 (m, 2H), 6.70 (broad s,1H), 3.57 (q,1H), 3.29 (dd,1H), 3.02–2.98 (m, 2H), 2.31–2.27 (m, 1H).

LC/MS: m/z 336.0 (M+1)

EXAMPLE 20

(±)-cis-1-(5-cyano-2-pyridinyl)-3-(2,5-difluoro-1,1a, 6,6a-tetrahydro-cyclopropa[a]inden-1-yl)-urea

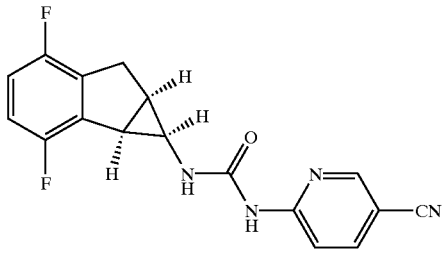

This compound was prepared analogously to Example 5e from (±)-cis-2,5-difluoro-1,1a,6,6a-tetrahydrocyclopropa[a] indene-1-carboxylic acid (60 mg, 0.28 mmol) and 2-amino-5-cyanopyridine (62 mg, 0.5 mmol) to give, after purification on silica gel (ethyl acetate and hexanes 2:1), 22 mg (29%) of the titled compound.

$^1$H-NMR (CDCl$_3$): 9.10 (s, 1H), 8.69 (s, 1H), 7.96 (s, 1H), 7.71 (dd, 1H), 6.90–6.77 (m, 3H), 3.63–3.55 (m, 1H), 3.29 (dd,1H), 3.03–2.96 (m, 2H), 2.29 (q, 1H).

LC/MS: m/z 327.0 (M+1)

Biological Results

Extensive guidance on the assay of test compounds at the enzyme level and in cell culture, including the isolation and/or selection of mutant HIV strains and mutant RT are found in DAIDS Virology Manual for HIV Laboratories complied by Division of AIDS, NIAID USA 1997. Resistance studies, including rational for various drug escape mutants is described in the HIV Resistance Collaborative Group Data Analysis Plan for Resistance Studies, revised Aug. 31, 1999.

Compounds of the invention are assayed for HIV activity, for example using multiple determinations with XTT in MT-4 cells (Weislow et al, J Nat Cancer Inst 1989, vol 81 no 8, 577 et seq), preferably including determinations in the presence of 40–50% human serum to indicate the contribution of protein binding. In short the XTT assay uses human T cell line MT4 cells grown in RPMI 1640 medium supplemented with 10% fetal calf serum (or 40–50% human serum as appropriate), penicillin and streptomycin seeded into 96 well microplates (2·10$^4$ cells/well) infected with 10–20 TCID$_{50}$ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a CO$_2$ enriched atmosphere and the viability of cells is determined at day five or six with XTT vital dye. Results are typically presented as ED$_{50}$ µM.

Compounds of the invention were assayed in the above XTT assay using wild type HIV-1$_{IIIB}$ as shown in Table 1

| Example | ED$_{50}$ (nM) |
| --- | --- |
| Example 5 | 9 |
| Example 6 | 36 |
| Example 8 | 32 |
| Example 9 | 44 |
| Example 17 | 42 |
| Example 19 | 10 |
| Example 20 | 14 |

Compounds are preferably potent against wild type virus and mutant HIV virus, especially virus comprising drug escape mutations. Drug escape mutations are those which arise in patients due to the selective pressure of a prior art antiviral and which confer enhanced resistance to that antiviral. The above cited Data Analysis Plan outlines relevant drug escape mutants for each of the antiviral classes currently on the market. Drug escape clones are readily isolated from HIV patients who are failing on a particular antiviral therapy. Alternatively the preparation of RT mutations on a known genetic background is shown in WO97/27319, WO99/61658 and WO00/73511 which also show the use of such mutants in sensitivity profiling.

What is claimed is:

1. A compound of the formula I:

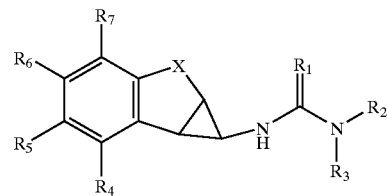

where;

R$_1$ is O, S;

R$_2$ is an optionally substituted, nitrogen-containing heterocycle, wherein the nitrogen is located at the 2 position relative to the (thio)urea bond;

R$_3$ is H, C$_1$–C$_3$ alkyl,

R$_4$–R$_7$ are independently selected from H, C$_1$–C$_6$ alkyl, C$_2$–C$_6$ alkenyl, C$_2$–C$_6$ alkynyl, haloC$_1$–C$_6$ alkyl, C$_1$–C$_6$ alkanoyl, haloC$_1$–C$_6$ alkanoyl, C$_1$–C$_6$ alkoxy, haloC$_1$–C$_6$ alkoxy, C$_1$–C$_6$ alkyloxy-C$_1$–C$_6$ alkyl, haloC$_1$–C$_6$ alkyloxy-C$_{1-C6}$ alkyl hydroxy-C$_1$–C$_6$ alkyl, amino-C$_1$–C$_6$ alkyl, carboxy-C$_1$–C$_6$ alkyl, cyano-C$_1$–C$_6$ alkyl, amino, carboxy, carbamoyl, cyano, halo, hydroxy, keto and the like;

X is —(CR$_8$R$_9$)$_n$—

$R_8$ and $R_9$ are independently H, $C_1$–$C_3$ alkyl, OH or $R_8$ and $R_9$ together are =O n is 1, 2 or 3
and prodrugs and pharmaceutically acceptable salts thereof.

2. A compound according to claim 1, wherein $R_1$ is O.

3. A compound according to claim 1, wherein $R_2$ is optionally substituted pyridyl or thiazoyl.

4. A compound according to claim 3, wherein $R_2$ is 5-substituted pyrid-2-yl.

5. A compound according to claim 4, wherein the 5-substituent is halo, cyano, phenoxy or ethynyl.

6. A compound according to claim 5 wherein the 5-substituent is bromo or chloro.

7. A compound according to claim 1, wherein $R_3$ is H.

8. A compound according to claim 1, wherein the cyclopropyl moiety has an enantiomeric excess of the conformation depicted in the partial formulae:

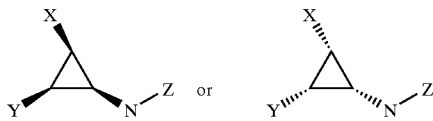

where X is as defined, Y is the bridge to the (substituted) phenyl ring depicted in formula I and Z is bond to the (thiourea)-$R_2$ depicted in formula I.

9. A compound according to claim 1 wherein the compound of formula I comprises an enantiomeric excess of the isomer showing negative optical activity.

10. A compound according to claim 1, wherein n is 1.

11. A compound according to claim 1, wherein n is 2.

12. A compound according to claim 1, wherein R4 is hydrogen, halo or hydroxy.

13. A compound according to claim 12, wherein R4 is fluoro.

14. A compound according to claim 1 wherein R5 is hydrogen, halo, $C_{1-3}$ alkylcarbonyl or C1–3alkyloxy.

15. A compound according to claim 14, wherein R5 is hydrogen or fluoro.

16. A compound according to claim 1, wherein R6 is hydrogen, halo, $C_1$–$C_3$alkyloxy, C1–3alkylcarbonyl, cyano or ethynyl.

17. A compound according to claim 16 wherein R6 is hydrogen, methoxy or fluoro.

18. A compound according to claim 1 wherein R7 is hydrogen, halo, $C_{1-3}$alkyloxy, or $C_{1-3}$alkylcarbonyl.

19. A compound according to claim 18, wherein R7 is fluoro.

20. A compound according to claim 1, wherein R5 and R6 are H and R4 and R7 are halo.

21. A compound according to claim 19, wherein R4 and R7 are fluoro.

22. A compound according to claim 21, wherein $R_1$ is O, n is 1, $R_3$ is H, and $R_2$ is substituted pyrid-2-yl.

23. A compound according to claim 21, wherein $R_1$ is S, n is 1, $R_3$ is H, and $R_2$ is substituted pyrid-2-yl.

24. A compound according to claim 21, wherein $R_1$ is O, n is 2, $R_3$ is H, and $R_2$ is 5-substituted pyrid-2-yl.

25. A compound according to claim 21, wherein $R_1$ is S, n is 1, $R_3$ is H, and $R_2$ is 5-substituted pyrid-2-yl.

26. A pharmaceutical composition comprising a compound as defined in any one of claims 1–25 and a pharmaceutically acceptable carrier or diluent therefor.

27. A method for the prevention or treatment of HIV infection in a human, the method comprising the administration of an effective amount of a compound as defined in claim 1 to the human.

28. A method according to claim 27, wherein the HIV is a drug escape mutant.

29. A method according to claim 28, wherein the drug escape mutant comprises the K1031 mutation.

* * * * *